US007344869B2

(12) United States Patent
Anders et al.

(10) Patent No.: US 7,344,869 B2
(45) Date of Patent: Mar. 18, 2008

(54) **ISOLATED DNA COMPRISING ONE OR MORE GENES SPECIFIC FOR 5S CLAVAM BIOSYNTHESIS, VECTORS COMPRISING SUCH DNA AND *STREPTOMYCES* HOSTS CAPABLE OF IMPROVED CLAVULANIC ACID PRODUCTION**

(75) Inventors: Cecilia Anders, Edmonton (CA); Barry Barton, Worthing (GB); John Patrick Griffin, Worthing (GB); Susan Jensen, Edmonton (CA); Roy Henry Mosher, Staten Island, NY (US); Ashish Sudhakar Paradkar, San Diego, CA (US)

(73) Assignees: SmithKline Beecham p.l.c., Brentford, Middlesex (GB); The Governors of the University of Alberta, Edmonton, Alberta (CA)

( * ) Notice: Subject to any disclaimer, the term of this patent is extended or adjusted under 35 U.S.C. 154(b) by 160 days.

(21) Appl. No.: 10/961,636

(22) Filed: Oct. 8, 2004

(65) Prior Publication Data

US 2007/0298470 A1 Dec. 27, 2007

Related U.S. Application Data

(62) Division of application No. 09/350,702, filed on Jul. 9, 1999, now Pat. No. 6,936,458, which is a division of application No. 09/018,806, filed on Feb. 4, 1998, now abandoned.

(30) Foreign Application Priority Data

Feb. 4, 1997 (GB) .................................... 9702218

(51) Int. Cl.
*C12P 7/40* (2006.01)
*C12N 1/21* (2006.01)
*C07H 21/04* (2006.01)

(52) U.S. Cl. ................. 435/136; 435/252.35; 536/23.2
(58) Field of Classification Search ..................... None
See application file for complete search history.

(56) References Cited

U.S. PATENT DOCUMENTS 4,202,819 A 5/1980 Kellett et al. ............... 540/347

FOREIGN PATENT DOCUMENTS

| CA | 2108113 | 4/1995 |
| EP | 0 550549 | 7/1993 |
| GB | 1 585 661 | 3/1981 |
| JP | 53-104796 | 9/1978 |

OTHER PUBLICATIONS

A.L. Demain, "Biosynthesis and Regulation of Beta-Lactam Antibiotics", In: 50 Years of Penicillin Applications, History & Trends (1990).
Townsend, et al., *J. Am. Chem. Soc.*, 107(4):1066-1068 (1985).
Valentine, et al., *J. Chem. Soc. Chem. Comm.*, 15:1210-1211 (1993).
Janc, et al., *Bioorg. Med. Chem. Lett.*, 3:2313-2316 (1993).
Rohl, et al., *Arch. Microbiol.*, 147:315-320 (1987).
Aidoo, et al., *Gene*, 147:41-46 (1994).
Sambrook, et al., Molecular Cloning: A Laboratory Manual, 2nd Edition. Cold Spring Harbor Laboratory, Cold Spring Harbor, NY (1989).
British Pharmacopoeia (1993); Addendum (1994) pp. 1362-1363.
British Pharmacopoeia Official Monographs, USP 23 NF18 pp. 384-385 (1985).
Hopwood, et al., Genetic Manipulation of *Streptomyces*. A Cloning Manual (1985).
Stahl, et al., In: Nucleic Acid Techniques in Bacterial Systematics. Ed. E. Stackebrandt & M. Goodfellow. Toronto: John Wiley & Sons, pp. 204-248 (1991).
Doran, et al., *J. Bacteriol.*, 172(9):4909-4918 (1990).
Vieira, et al., *Methods Enzymol.*, 153: 3-11 (1987).
Sanger, et al., *Proc. Natl. Acad. Sci. USA*, 74: 5463-5467 (1977).
Ward, et al., *Mol. Gen. Genet.* 203: 468-478 (1986).
Pruess, et al., *The Journal of Antibiotics*, XXXVI(3): 208-212 (1983).
Paradkar, et al., *Journal of Bacteriology*, 177: 1307-1314 (1995).
Hodgson, J.E. et al., *Gene*, (1995) vol. 166, pp. 49-55.
Busby, R.W., *J. Biological Chem.*, (1995), vol. 270(9), pp. 4262-4269.
Brown, D. et al., *J.C.S. Chem. Comm.*, (1979), pp. 282-283.
Marsh, E.N. et al., *Biochemistry*, (1992), vol. 31, pp. 12648-12657.
Elson, et al. *J. Antibiotics*, XXXI(6): 568 (1978).
Evans, R. H. et al., *J. Antiobiotics*, (1983), vol. 36(3), pp. 213-216.
Muller, J-C. et al, *J. Antiobiotics*, (1983), vol. 36(3), pp. 216-224.
King, H.D. et al., *J. Antiobiotics*, (1986), vol. 39(4), pp. 510-515.
Janc, J.W. et al., *J. Biological Chem.*, (1995), vol. 270(10), pp. 5399-5404.
Iwata-Reuly, D. and C. A. Townsend, *J. Am. Chem. Soc.*, (1992), vol. 114, pp. 2762-2763.
Paradkar, A. S. and S. E. Jensen, *J. Bacteriology*, (1995), vol. 177(5), pp. 1307-1314.
Baldwin, J. E. et al., *Tetrahedron Letters*, (1994), vol. 35(17), pp. 2783-2786.
Egan, L.A. et al., *J. AM. Chem. Soc.*, (1997), vol. 119, pp. 2348-2355.

*Primary Examiner*—Elizabeth Slobodyansky
(74) *Attorney, Agent, or Firm*—Andrea V. Lockenour; Jeffrey A. Sutton

(57) ABSTRACT

Novel bacterial genes, microorganisms and processes for improving the manufacture of 5R clavams, eg. clavulanic acid.

3 Claims, 9 Drawing Sheets

Figure 1

```
           NcoI       .           .           .           .           .           .
    1  GGTACCGCCCGCCGCCGACGGGGCCTCGGAGCCGGCCTGGCCACTGGTCCTGGTGGGGCC    60
          M  A  P  P  P  Q  G  P  A  E  A  P  G  T  V  L  V  V  G

.           .           .           .           .           .
   61  ACCCTATCACCGGGCGGTGGGCCGCGTCGTCTGAGGGCCTGTGCCTGGGCACCCACACGC   120
        T  P  Y  H  G  A  V  R  R  L  L  S  G  S  V  S  G  H  T  H

.           <orfup3     .           .           .
  121  GCCTTTCCGGGCCTCCGGCCCAGTGTCGGTGCCCATTGCGCGCCACAGGAACGGGCGCAT   180
                                 *  L  W  P  Y  R  A  T  D  K  G  A  Y
        A  S  L  G  P  P  R  T  M .           .           .           .           .           .
  181  TAGCCCCAGGTCTATCTGCTTCCGGGCCACCTGCTCCTTCAGGGCGTGGAGCATCTGGCA   240
           D  P  D  L  Y  V  F  A  R  H  V  L  F  D  R  V  E  Y  V  T .           .           .           .           .           .
  241  CGTGGTCGCGGGCCGCCGGGTGAGCCCCAGTGGGCGGGCGGTGCCGGGCAGGGCCACGAG   300
           C  W  R  G  A  A  W  E  P  D  G  A  R  W  P  G  D  R  H  E .           .           .           .           .           .
  301  TGGCACCCACCACGGGAGGCGCCGCTCCTCAAGCCAGGGCCAGTCTTAGGTCAACTGCCT   360
           G  H  T  T  G  E  A  A  L  L  E  T  G  T  L  I  W  N  V  S .           .           .           .           .           .
  361  GGTGTCTACCACCCACTAGCTCGCCTACCACGGGGGCTCCAGCAGCTTCTCGGCCCGCTA   420
           W  L  H  H  T  I  S  R  I  T  G  G  L  D  D  F  L  R  A  I .           .           .           .           .           .
  421  GAGCCTGAACGGGGCCCGGTCTGGGGTGAACCCCTTCTTCTTCTGGCGCAGGAGCCGCTT   480
           E  S  K  G  R  A  L  G  W  K  P  F  F  F  V  A  D  E  A  F .           .           .           .           .           .
  481  CATCAGCTAGCGCCCCCACGGCAGCGACGGCTGCGGCGGCAACAGCTTGCGGAACTTCAT   540
           Y  D  I  A  P  T  G  D  S  G  V  G  G  N  D  F  A  K  F  Y .           .           .           .           .     <orfup2
  541  GCGCCACTACTGGCGGAACGCGACGAGCAGGCAGTATGGCCGGCTACGGTGCCTGTACTT   600
           A  T  I  V  A  K  R  Q  E  D  T  M  G  A  S  A  V  S  M .           .           .           .           .           .
  601  TGCTGGAGGTCTCTAAGGCCCACCGACACGACCCCGACGCCTTCCCCACAGGGGCGCTT    660

.           .           .           .           .           .
  661  CCTGCCGCCTGCGGCGCCTGCGGCGCCGGCAGAGGGGCCGCCTGCCCAGGGTCGCAGGAC   720

.           .           .           .           .           .
  721  CTCTCCCGAACCGCCGCCGAACTGCGGCACGACAGGGCGCCGAACGCCTTGCGCTTCATG   780

.           .           .           .           .           .
  781  GCCGGTCGCATGCCCGCAACGTGGCCTGCACATGCGGCCAGCCCTGGGGAGCATGGGGGC   840
                   .           .           .           .           .           .
```

Figure 1 continued

```
 841  CTCGGCCGGCTGGGGCCGCCGAGGCCCCCATGCCTGCGCGGCCTGGCCGGGCTCGCTCGG   900

901  CCTGCCCAGCCTGCCACGCGCACCAAGGCCACACAGCCTGTCGAGCCTGCCTGGCCTGCC   960

961  ACGCGCACCAAGGCCACACAGCCTGTCGAGCCTGCCCAGCCTGCCACGCGCACCAAGGCC  1020

1021  GTGCGGCCTGCCCAGTCAACGGCTAGTACCGCTCGTTACGGCCCCACATGGCGAGGGGCC  1080
                     *  N  G  I  M  A  L  L  A  P  T  Y  R  E  G

1081  TGTGGCCCACCCTCTAGCGCCGGCAGTGGAGGCGCTCCCTGGCCAGCAGGTCGGCCTAGC  1140
       S  V  P  H  S  I  A  A  T  V  E  A  L  S  R  D  D  L  R  I

1141  TCCGCCGCCGCTCTAACAGGCGCTCTACCCGGCCCAAGCGCCACGGGCCCTAGCCCTGCT  1200
       S  A  A  A  L  N  D  A  L  H  A  P  N  A  T  G  P  I  P  V

1201  GCAGGAGCGGGGCCACCACGTCGGTCCGCTCGCGCTCGACACGGTCCCAGTCGGGGTCTG  1260
       V  D  E  G  R  H  H  L  W  A  L  Q  A  L  T  L  G  L

1261  GCAGGCGCTGGCCCGCGTCGGCCACGTCGTTGCTCGCCAACGCGCGCTCCCGGCCTCGCG  1320
       G  D  A  V  P  R  L  R  H  L  L  S  R  N  R  A  L  A  P  A

1321  ACTTGGCCCCGACCGGGGCCGCCTTCAGGAGCAGGGGGTCTAGCAGCCACCACGCCTACC  1380
       S  F  R  P  Q  G  R  R  F  D  E  D  G  L  D  D  T  T  R  I

1381  ACGGCCACTCTTTTGGGGCAGGGTCTCCCCGCATTCGCTGCTAGGGCTAGGGGTCGAGGG  1440
       T  G  T  L  F  G  R  G  L  P  A  Y  A  V  I  G  I  G  L  E

1441  CCGTCTGCCCGTGGTGGAGCAGGAGCTAGGGCGCGCTGGTGTCCGAGGTGAGCGAGACGT  1500
       R  C  V  P  V  V  E  D  E  I  G  R  S  W  L  S  W  E  S  Q

1501  GGCGGCAGTGGCCCACGTGGCGCAGGCGGGCCGCGTCGCACCGGCGCCTCCCGAGCCTCT  1560
       V  A  T  V  P  H  V  A  D  A  R  R  L  T  A  A  S  P  E  S

1561  CTGGCTCGGACGCCTGGAACGGGAGCGCGTGGTCGAGCCGGTGGCGTGGGTGCCAGAGGA  1620
       L  G  L  R  R  V  K  G  E  R  V  L  E  A  V  A  G  V  T  E

1621  GCTAGCCGTGGCGGCCCAGGCAGGTCACGACCATCATGTCCAGCTACGCCAGCCACGGCT  1680
       E  I  P  V  A  P  D  T  W  H  Q  Y  Y  L  D  I  R  D  T  G

1681  CTGCTGCGTCCCTGGCAAGCGTCCGGCGCGCCTGCATCCTGCCGAGCGGCGTGTTCGGGA  1740
       L  R  R  L  S  R  E  C  A  A  R  V  Y  S  P  E  G  C  L  G

1741  CCCTCCGCGGCAGCCTGCTCGCGTGGTACGGCTTGAACCACCGCTAGTCGTGGAGCAGGG  1800
       Q  S  A  G  D  S  S  R  V  M  G  F  K  T  A  I  L  V  E  D
```

Figure 1 continued

```
1801 CCGCCGGGCGCTGGCGGGCAGGCTCGTCGAGGAGTGGCCGCGGCTCGGGGACCTGCAGCC 1860
      R  R  G  A  V  A  R  G  L  L  E  E  G  A  G  L  G  Q  V  D

1861 GCCACAGGTCGTCCCACTGGGGCCGCAGCTGCCGCCGCGCCTACCACCGGCAGCGGGCCC 1920
      A  T  D  L  L  T  V  G  A  D  V  A  A  R  I  T  A  T  A  R

1921 GCGCCAGGCCCGCAGGCATCTTCAGCCACCAGCCGTCCGTCGGCTCGGGGACCCGTGACT 1980
      A  R  D  P  R  G  Y  F  D  T  T  P  L  C  G  L  G  Q  A  S

1981 GGCCTTCCAGGGCGTCCCGCGCCTGGCCGCCTGCGCCTTGGCGCCGCCTGTGCCTTGGCC 2040
      V  P  L  D  R  L  A  R  V  P  P  R  P  V  A  A  S  V  S  G

<orfup1
2041 CCGGGGACTCGGGCGGAGAGCGGGACATACGGAACCTCCACAGGCGGAGCCGGGAACGGG 2100
     GGCCCCTGAGCCCGCCTCTCGCCCTGTATGCCTTGGAGGTGTCCGCCTCGGCCCTTGCCC
      A  P  S  E  P  P  S  R  S  M 2101 ACGAGGGCGAGGACGGGACGGAACGAAGGAGAGGACGGGACGGACAGCACGGACGGGACG 2160
     TGCTCCCGCTCCTGCCCTGCCTTGCTTCCTCTCCTGCCCTGCCTGTCGTGCCTGCCCTGC 2161 GACGGAACGGAGTCGGGAACCGGGGGGGGTGACCGGAACCGGGCCGTCCTTGGCCCTCCC 2220
     CTGCCTTGCCTCAGCCCTTGGCCCCCCCCACTGGCCTTGGCCCGGCAGGAACCGGGAGGG 2221 CCGTCCTCCCCGCCATCCGCCGTTCTCCCCCGTTCCCTCTCCCGTCCTCCAGCCAACACC 2280
     GGCAGGAGGGGCGGTAGGCGGCAAGAGGGGGCAAGGGAGAGGGCAGGAGGTCGGTTGTGG 2281 GCCGCCCTTTCCAAGCGCTTGACACGGCACCGACAGCCGCCGCCGGGCGCCCGATGGGGA 2340
     CGGCGGGAAAGGTTCGCGAACTGTGCCGTGGCTGTCGGCGGCGGCCCGCGGGCTACCCCT 2341 CCCGTGCCCGCCGGTGAGCGGCGGTGAGCGCCGGTACGGGACCCCACGCGCCGCCGCCCG 2400
     GGGCACGGGCGGCCACTCGCCGCCACTCGCGGCCATGCCCTGGGGTGCGCGGCGGCGGGC 2401 GGCGCCCGCCAGGGCCCGCGCGGCCACCCCGGCCCGCCCCGGCCGGAGCGGCGATCCGGG 2460
     CCGCGGGCGGTCCCGGGCGCGCCGGTGGGGCCGGGCGGGGCCGGCCTCGCCGCTAGGCCC 2461 CCGCTCGCTGCAAGAGGAACATCCACAGCCGCACAAGGAGCGCTCCGCACAGTGGGCACC 2520
     GGCGAGCGACGTTCTCCTTGTAGGTGTCGGCGTGTTCCTCGCGAGGCGTGTCACCCGTGG 2521 ACGTCCGCCCCGTCCCCCACACCGTGGCCGGTCCCCACCGGACAGCACAGCACCGCACAG 2580
     TGCAGGCGGGGCAGGGGGTGTGGCACCGGCCAGGGGTGGCCTGTCGTGTCGTGGCGTGTC

2581 CACCACATCGCACGGCACAGCACAGCACCACCGGCACGAGGAACCAAGGAAAGGAACCAC 2640
```

Figure 1 continued

```
          GTGGTGTAGCGTGCCGTGTCGTGTCGTGGTGGCCGTGCTCCTTGGTTCCTTTCCTTGGTG cas1>
               M  T  S  V  D  C  T  A  Y  G  P  E  L  R  A  L  A  A
     2641  ACCACCATGACCTCAGTGGACTGCACCGCGTACGGCCCCGAGCTGCGCGCGCTCGCCGCC  2700
               TGGTGGTACTGGAGTCACCTGACGTGGCGCATGCCGGGGCTCGACGCGCGCGAGCGGCGG 2701  CGGCTGCCCCGGACCCCCCGGGCCGACCTGTACGCCTTCCTGGACGCCGCGCACACAGCC  2760
            R  L  P  R  T  P  R  A  D  L  Y  A  F  L  D  A  A  H  T  A 2761  GCCGCCTCGCTCCCCGGCGCCCTCGCCACCGCGCTGGACACCTTCAACGCCGAGGGCAGC  2820
            A  A  S  L  P  G  A  L  A  T  A  L  D  T  F  N  A  E  G  S 2821  GAGGACGGCCATCTGCTGCTGCGCGGCCTCCCGGTGGAGGCCGACGCCGACCTCCCCACC  2880
            E  D  G  H  L  L  L  R  G  L  P  V  E  A  D  A  D  L  P  T NcoI
     2881  ACCCCGAGCAGCACCCCGGCGCCCGAGGACCGCTCCCTGCTGACCATGGAGGCCATGCTC  2940
            T  P  S  S  T  P  A  P  E  D  R  S  L  L  T  M  E  A  M  L KpnI.
     2941  GGACTGGTGGGCCGCCGGCTCGGTCTGCACACGGGGTACCGGGAGCTGCGCTCGGGCACG  3000
            G  L  V  G  R  R  L  G  L  H  T  G  Y  R  E  L  R  S  G  T 3001  GTCTACCACGACGTGTACCCGTCGCCCGGCGCGCACCACCTGTCCTCGGAGACCTCCGAG  3060
            V  Y  H  D  V  Y  P  S  P  G  A  H  H  L  S  S  E  T  S  E 3061  ACGCTGCTGGAGTTCCACACGGAGATGGCCTACCACCGGCTCCAGCCGAACTACGTCATG  3120
            T  L  L  E  F  H  T  E  M  A  Y  H  R  L  Q  P  N  Y  V  M 3121  CTGGCCTGCTCCCGGGCCGACCACGAGCGCACGGCGGCCACACTCGTCGCCTCGGTCCGC  3180
            L  A  C  S  R  A  D  H  E  R  T  A  A  T  L  V  A  S  V  R 3181  AAGGCGCTGCCCCTGCTGGACGAGAGGACCCGGGCCCGGCTCCTCGACCGGAGGATGCCC  3240
            K  A  L  P  L  L  D  E  R  T  R  A  R  L  L  D  R  R  M  P 3241  TGCTGCGTGGATGTGGCCTTCCGCGGCGGGGTGGACGACCCGGGCGCCATCGCCCAGGTC  3300
            C  C  V  D  V  A  F  R  G  G  V  D  D  P  G  A  I  A  Q  V 3301  AAACCGCTCTACGGGGACGCGGACGATCCCTTCCTCGGGTACGACCGCGAGCTGCTGGCG  3360
            K  P  L  Y  G  D  A  D  D  P  F  L  G  Y  D  R  E  L  L  A 3361  CCGGAGGACCCCGCGGACAAGGAGGCCGTCGCCGCCCTGTCCAAGGCGCTCGACGAGGTC  3420
            P  E  D  P  A  D  K  E  A  V  A  A  L  S  K  A  L  D  E  V
```

Figure 1 continued

```
3421 ACGGAGGCGGTGTATCTGGAGCCCGGCGATCTGCTGATCGTCGACAACTTCCGCACCACG 3480
      T  E  A  V  Y  L  E  P  G  D  L  L  I  V  D  N  F  R  T  T

3481 CACGCGCGGACGCCGTTCTCGCCCCGCTGGGACGGGAAGGACCGCTGGCTGCACCGCGTC 3540
      H  A  R  T  P  F  S  P  R  W  D  G  K  D  R  W  L  H  R  V

3541 TACATCCGCACCGACCGCAATGGACAGCTCTCCGGCGGCGAGCGCGCGGGCGACGTCGTC 3600
      Y  I  R  T  D  R  N  G  Q  L  S  G  G  E  R  A  G  D  V  V

A  F  T  P  R  G  *  SacI
3601 GCCTTCACACCGCGCGGCTGAGCTCCCGGGTCCGACACCGCGCGGCTGAACCCACGGTCC 3660
     CGGAAGTGTGGCGCGCCGACTCGAGGGCCCAGGCTGTGGCGCGCCGACTTGGGTGCCAGG

3661 GGGGCCCACGGTCCGGCACCGCGCGGCTGAGCCCCCGGGTCCGGCAGCGGGCGGCTGAAC 3720
     CCCCGGGTGCCAGGCCGTGGCGCGCCGACTCGGGGGCCCAGGCCGTCGCCCGCCGACTTG

3721 CCCCGCCCCGGGCCACCGCCCGACCGCCCCGCGCACCGGACGCGCCCGCCTGTACGGCG 3780
     GGGGCGGGGCCCGGTGGCGGGCTGGCGGGGGCGCGTGGCCTGCGCGGGCGGACATGCCGC

3781 GTCCCGCCCGGGCCCGTACACCTGAAGCGCCCGGCGGACCGCCGCCCCGCCGGGGACGG 3840
     CAGGGCGGGCCCGGGCATGTGGACTTCGCGGGCCGCCTGGCGGCGGGGCGGCCCCCTGCC

---------------->   <------------------
3841 ACAGAGCCGGGTGCGGGAGGACGTCCTCCCGCACCCGGCTCCCACCGTTCCGCACCGACC 3900
     TGTCTCGGCCCACGCCCTCCTGCAGGAGGGCGTGGGCCGAGGGTGGCAAGGCGTGGCTGG

3901 GCACCCGACCGTGCCGCAGGCGCCACCGGCACCGCACCGCCCGCGCCGGCAGCCACCACA 3960
     CGTGGGCTGGCACGGCGTCCGCGGTGGCCGTGGCGTGGCGGGCGCGGCCGTCGGTGGTGT

3961 GGCGCCACGCCGCCCGCACGGTGCCCGCGCTGCTCAGCCCCCGTCCACCGGGCTGTCCAG 4020
     CCGCGGTGCGGCGGGCGTGCCACGGGCGCGACGAGTCGGGGGCAGGTGGCCCGACAGGTC
                                          *  G  G  D  V  P  S  D  L

4021 GTCGGCGGCGTCGCGCGGGGGCTACTTGAGGGCCAGCCGCCGGCTGGGGGGCCTGGGGCG 4080
      L  R  R  L  A  G  G  I  F  E  R  D  A  A  S  G  G  S  G  A

4081 CTCTACGGGGGTGTGAGGGCCCTAGTGGAGGTCGCTCCGTATGCCGTCGTCTAGCCGGTG 4140
      L  H  G  W  V  G  P  I  V  E  L  S  A  Y  P  L  L  D  A  V

4141 GGCGAAGAGCAGGAGCTGCCGCTTTGTGTGCAGGTCCCGCGGGCCGTCGTGGTGCCGGGC 4200
      R  K  E  D  E  V  A  F  C  V  D  L  A  G  P  L  V  V  A  R

4201 GCGGCACTGCCTCCGGTCGCGGCGGAGCTGCGAGGGGGGCCGGGGCCCACAGCGGGGGTG 4260
```

NcoI
4261  TAGGCACAAGAGGGTCCACGCGTGGTACCACTCGTCTAGGCGCCGCGGCCCGGGCCTCTC  4320
        D   T   N   E   W   T   R   V   M   T   L   L   D   A   A   G   P   G   S   L

4321  CTTCTGGACGAGGGTCTTCGGCCACTCCATGAGGAGCGCCCACCGCTTTGGGTCGAGGGC  4380
        F   V   Q   E   W   F   G   T   L   Y   E   E   R   T   A   F   G   L   E   R

4381  CACCCGTGCCGCCCGGGTCTTCCTTGCGCTCCAGGGGGTGGGCCGCTTGTGGGCCGGGCG  4440
        H   A   R   R   A   W   F   S   R   S   T   G   W   G   A   F   V   R   G   A

4441  GCGGAAGGCGGGGGCGAGGGGCCGCAGCCGCGACTCGCGGCGCCGGTCTGGCCTGTCGTC  4500
        A   K   R   G   R   E   G   A   D   A   S   L   A   A   A   L   G   S   L   L

4501  CTGGTCCGACACGCCCGACGAGTGGCCGCGGGGCGTCTAGCCCCGCTAGGCCGCGTGGTA  4560
        V   L   S   H   P   S   S   V   P   A   G   C   I   P   A   I   R   R   V   M

4561  GGGGCCTACGCTGTGCCGGGTGACCATCCGCACCCGGCGCGGGTAGCTGGTCGGGCACTG  4620
        G   P   H   S   V   A   W   Q   Y   A   H   A   A   G   M   S   W   G   T   V

4621  GTCCCGGTCAAGGGCATGGGGGTCGAGGAGCCACTCGTCGGCCACGACGCGGCGCTGTAA  4680
        L   A   L   E   R   V   G   L   E   E   T   L   L   R   H   Q   A   A   V   N

4681  CAGGACGCCTCACTAGTCGCCTTTCGCCCTGGGGCTGCCCACCAACGGCCCGCTCGACCT  4740
        D   Q   P   T   I   L   P   F   R   S   G   S   P   H   N   G   P   S   S   S

4741  CTGGGGCAACGGCTTCTCAGGCCGCCACTGCTGCGTCATGGCGGCCCACAGGTCGCCGTC  4800
        V   G   N   G   F   L   G   A   T   V   V   C   Y   R   R   T   D   L   P   L

4801  GGGGCGTGGCTAGTCGGTCAGCATGGGCCACACCAGGGCCGGCTTCTTGCTGCCTGTCTC  4860
        G   A   G   I   L   W   D   Y   G   T   H   D   R   G   F   F   S   P   C   L

4861  GTGGTGCAAGCAGGGCAGCCGCAAGCCGCACGGCATGTACCGCATTGGCTAGGCCCGCAG  4920
        V   V   N   T   G   D   A   N   P   T   G   Y   M   A   Y   G   I   R   A   D

<orfdwn1
4921  GGCGTCCTGGAGGGGCAGGTCGTTGCCGTCAAGCAGCTAGAGCTTATACGCCGTAAGGTG  4980
        R   L   V   E   G   D   L   L   P   L   E   D   I   E   F   I   R   C   E   M 4981  GCGACTGGAGGAACAAGCTAGGGGGGCCTGTTGTCCAGCCAGCACCGGCCTCTGAGTCTC  5040
                                                              *   L
```

Figure 1 continued

```
5041 GGTCAACCCCGCTAGAGCCACCGGGTGTCGAGGTCCGACGCGTCGACCTGTAGCACGCC 5100
      W  N  P  A  I  E  T  A  W  L  E  L  S  R  L  Q  V  D  H  P

5101 CTAGTCGGGCCTCATGACCGTGACCTCGTCTATGAGGCCTAGCACGGCGAGGTGGTCGAA 5160
      I  L  G  S  Y  Q  C  Q  L  L  Y  E  P  D  H  R  E  V  L  K

5161 GAGCTAGTACGCCAACTACAGCAGGCCCCACGGCTGGGTGAGGTCGGGGGCCAGCTGGTC 5220
      E  I  M  R  N  I  D  D  P  T  G  V  W  E  L  G  R  D  V  L

5221 CCAGAACATCAGGCTCGGCTAGCCTGGGCAGAGCGGCCAGCGCGCGTCGCGGAGCCACTT 5280
      T  K  Y  D  S  G  I  P  G  T  E  G  T  A  R  L  A  E  T  F

NcoI
5281 CGGGTACCCCGGCTTGGTCAAGAGCTTCTACTTCGGCGGCGGCGCCCTGCGGGTCACCAC 5340
      G  M  P  G  F  W  N  E  F  I  F  G  G  G  R  S  A  W  H  H

5341 CCGGAGCGGCCTCAGGGCCCTCTGGTCCTGCAGGAAGTAGTGGGGCTGGGCGAGCGGGGC 5400
      A  E  G  S  D  R  S  V  L  V  D  K  M  V  G  V  R  E  G  R

5401 GGCGTCCCACGGCACCGGGCGGCGGAGCCGGAGGAGGGCCATCTACAGGTAGTCGGCCCG 5460
      R  L  T  G  H  G  A  A  E  A  E  E  R  Y  I  D  M  L  R  A

5461 CTGCTAGACCAGCAGCCACAAGTAGTCCTAGCCGTGGTGCGGGAGGGCCCGTGTCTTGGC 5520
      V  I  Q  D  D  T  N  M  L  I  P  V  V  G  E  R  A  C  F  R

5521 CTTGCACAGGAGTGACTTCGACTTGCCGACCTTCTGCCCGCCCACCCCCGCGACCATCCC 5580
      F  T  D  E  S  F  S  F  P  Q  F  V  P  P  H  P  R  Q  Y  P

5581 GAACCCGCGCTACGGGTGGAGCGCCTACTGCGGCAAGAGCAGCTCCGGGGCCGGCATCGC 5640
      K  P  A  I  G  V  E  R  I  V  G  N  E  D  L  G  R  G  Y  R

5641 CGCGTGGCGGAGCATCCCCTTGAGGTCCAGGCCGTGGCCCTAGCAGGTGACGAGGGGCCT 5700
      R  V  A  E  Y  P  F  E  L  D  P  V  P  I  T  W  Q  E  G  S

5701 CACCCACTTGCAGAGCCAGCAGGTGCGGAAGAACTACTAGAGGGTCACGAGGAGCTTCTC 5760
      H  T  F  T  E  T  T  W  A  K  K  I  I  E  W  H  E  E  F  L

5761 CCGTGCTAACGCGGCCAGGGCGAGGGGCCGCAGCCTGTCCCACGGCGGCTGGGGCATGTG 5820
      A  R  N  R  R  D  R  E  G  A  D  S  L  T  G  G  V  G  Y  V

5821 GACGGGGTACTACAGCCGGGTCGCGAAGACCTTGGGCGCGCGCTAGGGCTGCTTCCGCGC 5880
      Q  G  M  I  D  A  W  R  K  Q  F  G  R  A  I  G  V  F  A  R

5881 CGGGGCCCAGTACACCAGCTCGTAGCGGTCTAGGAGCCGGTCGGCGTCGCCTAACACGTC 5940
```

Figure 1 continued

```
                  G  R  T  M  H  D  L  M  A  L  D  E  A  L  R  L  P  N  H  L
5941 GCCGTCCTGCAACCGGTAGACCGGCTGGGCCTACACGGCCCAGACGTACGGCTCCATCTC 6000
        P  L  V  N  A  M  Q  G  V  R  I  H  R  T  Q  M  G  L  Y  L

6001 GGGGTCGTACTAGCCCAACAACCTCTGGAGCTTTGGGAGCCACACCTTCACCACGAGCCA 6060
        G  L  M  I  P  N  N  S  V  E  F  G  E  T  H  F  H  H  E  T

6061 CTTCCTGTCAGGGGTCATCGGCTCAAGCAGCCGGCGGACGCGGACGGCCCACTCGACGGC 6120
        F  S  L  G  W  Y  G  L  E  D  A  A  Q  A  Q  R  T  L  Q  R

6121 CTCGTACAAGACCATCAAGACGCCTAACTGGGGGCGGTATGGGGCGACCTGGACGCGTAC 6180
        L  M  N  Q  Y  N  Q  P  N  V  G  A  M  G  R  Q  V  Q  A  H

<orfdwn2
6181 ACTGCCGACCGTTGGCAGATAGAAGAGAATGGACTTCACCCTGGCTCCTCCGGTTCGCGG 6240
     TGACGGCTGGCAACCGTCTATCTTCTCTTACCTGAAGTGGGACCGAGGAGGCCAAGCGCC
                              S  G  V  T  P  L  Y  F  L  I  S  K  M 6241 CGCCCTCCATTGACGTGCGCCGAAAGCGGCTCGACCGTCCCACTCCGCCCTTGAGTTCCG 6300
     GCGGGAGGTAACTGCACGCGGCTTTCGCCGAGCTGGCAGGGTGAGGCGGGAACTCAAGGC 6301 TCTGACGCCGCGCCAGTCGGCGGGCCGTCCGCCGGGGTGCCCGCCGGGGTCCGCACCCGC 6360
     AGACTGCGGCGCGGTCAGCCGCCCGGCAGGCGGCCCCACGGGCGGCCCCAGGCGTGGGCG 6361 CGGACGGCACGGCGCGCACCGCGCGCGCGGCGCTTCGGGGCACCGGGCTCGACGGGGTGC 6420
     GCCTGCCGTGCCGCGCGTGGCGCGCGCCGCGAAGCCCCGTGGCCCGAGCTGCCCCACG 6421 TCAGCGGGACGTCCAACGGAAGGCAAGCCCCCGTACCCAGCCTGGTCAAGGCGCTCATCG 6480
     AGTCGCCCTGCAGGTTGCCTTCCGTTCGGGGGCATGGGTCGGACCAGTTCCGCGAGTAGC orfdwn3>
                                                .  M  P  G
6481 CCATTCCCTGAGGAGGTCCCGCCTTGACCACAGCAATCTCCGCGCTCCCGACCGTGCCCG 6540
     GGTAAGGGACTCCTCCAGGGCGGAACTGGTGTCGTTAGAGGCGCGAGGGCTGGCACGGGC 6541 GCTCCGGACTCGAAGCACTGGACCGTGCCACCCTCATCCACCCCACCCTCTCCGGAAACA 6600
        S  G  L  E  A  L  D  R  A  T  L  I  H  P  T  L  S  G  N  T 6601 CCGCGGAACGGATCGTGCTGACCTCGGGGTCCGGCAGCCGGGTCCGCGACACCGACGGCC 6660
        A  E  R  I  V  L  T  S  G  S  G  S  R  V  R  D  T  D  G  R 6661 GGGAGTACCTGGACGCGAGCGCCGTCCTCGGGGTGACCCAGGTGGGCCACGGCCGGGCCG 6720
        E  Y  L  D  A  S  A  V  L  G  V  T  Q  V  G  H  G  R  A  E
```

Figure 1 continued

```
6721 AGCTGGCCCGGGTCGCGGCCGAGCAGATGGCCCGGCTGGAGTACTTCCACACCTGGGGGA 6780
      L  A  R  V  A  A  E  Q  M  A  R  L  E  Y  F  H  T  W  G  T

6781 CGATCAGCAACGACCGGGCGGTGGAGCTGGCGGCACGGCTGGTGGGGCTGAGCCCGGAGC 6840
      I  S  N  D  R  A  V  E  L  A  A  R  L  V  G  L  S  P  E  P

6841 CGCTGACCCGCGTCTACTTCACCAGCGGCGGGGCCGAGGGCAACGAGATCGCCCTGCGGA 6900
      L  T  R  V  Y  F  T  S  G  G  A  E  G  N  E  I  A  L  R  M

6901 TGGCCCGGCTCTACCACCACCGGCGCGGGGAGTCCGCCCGTACCTGGATACTCTCCCGCC 6960
      A  R  L  Y  H  H  R  R  G  E  S  A  R  T  W  I  L  S  R  R

6961 GGTCGGCCTACCACGGCGTCGGATACGGCAGCGGCGGCGTCACCGGCTTCCCCGCCTACC 7020
      S  A  Y  H  G  V  G  Y  G  S  G  G  V  T  G  F  P  A  Y  H

7021 ACCAGGGCTTCGGCCCCTCCCTCCCGGACGTCGACTTCCTGACCCCGCCGCAGCCCTACC 7080
      Q  G  F  G  P  S  L  P  D  V  D  F  L  T  P  P  Q  P  Y  R

7081 GCCGGGAGCTGTTCGCCGGTTCCGACGTCACCGACTTCTGCCTCGCCGAACTGCGCGAGA 7140
      R  E  L  F  A  G  S  D  V  T  D  F  C  L  A  E  L  R  E  T
                                                         Sau
7141 CCATCGACCGGATCGGCCCGGAGCGGATCGCGGCGATGATCGGCGAGCCGATC
      I  D  R  I  G  P  E  R  I  A  A  M  I  G  E  P  I
```

ISOLATED DNA COMPRISING ONE OR MORE GENES SPECIFIC FOR 5S CLAVAM BIOSYNTHESIS, VECTORS COMPRISING SUCH DNA AND *STREPTOMYCES* HOSTS CAPABLE OF IMPROVED CLAVULANIC ACID PRODUCTION

This is a divisional of patent application Ser. No. 09/350,702 filed 9 Jul. 1999 now U.S. Pat. No. 6,936,458, (RCE filed Aug. 16, 2004), which is a divisional of application Ser. No. 09/018,806 filed Feb. 4, 1998, now abandoned, which claims priority to Great Britain application GB9702218.0 filed Feb. 4, 1997.

FIELD OF INVENTION

The present invention relates to novel bacterial genes and processes for improving the manufacture of clavams e.g. clavulanic acid. The present invention also provides novel organisms capable of producing increased amounts of clavulanic acid.

BACKGROUND OF THE INVENTION

Microorganisms, in particular *Streptomyces* sp. produce a number of antibiotics including clavulanic acid and other clavams, cephalosporins, polyketides, cephamycins, tunicamycin, holomycin and penicillins. There is considerable interest in being able to manipulate the absolute and relative amounts of these antibiotics produced by the microorganism and accordingly there have been a large number of studies investigating the metabolic and genetic mechanisms of the biosynthetic pathways [Domain, A. L. (1990) "Biosynthesis and regulation of beta-lactam antibiotics." In: 50 years of Penicillin applications, history and trends]. Many of the enzymes which carry out the various steps in the metabolic pathways and the genes which code for these enzymes are known.

Clavams can be arbitrarily divided into two groups dependent on their ring stereochemistry (5S and 5R clavams). The biochemical pathways for the biosynthesis of 5R and 5S clavams have not yet been fully elucidated but it has been suggested that they are derived from the same starter units (an as yet unidentified 3 carbon compound [Townsend, C. A. and Ho, M. F. (1985) J. Am. Chem. Soc. 107 (4), 1066-1068 and Elson, S. W. and Oliver, R. S. (1978) J. Antibiotics XXXI No. 6, 568] and arginine [Valentine, B. P. et al (1993) J. Am. Chem. Soc. 15, 1210-1211] and share some common intermediates [Iwata-Reuyl, D. and C. A. Townsend (1992) J. Am. Chem. Soc. 114: 2762-63, and Janc, J. W. et al (1993) Bioorg. Med. Chem. Lett. 3:2313-16].

Examples of 5S clavams include clavam-2-carboxylate (C2C), 2-hydroxymethylclavam (2HMC), 2-(3-alanyl)clavam, valclavam and clavaminic acid [GB 1585661, Rohl, F. et al. Arch. Microbiol. 147:315-320, U.S. Pat. No. 4,202,819] There are, however, few examples of 5R clavams and by far the most well known is the beta lactamase inhibitor clavulanic acid which is produced by the fermentation of *Streptomyces clavuligerus*. Clavulanic acid, in the form of potassium clavulanate is combined with the beta-lactam amoxycillin in the antibiotic AUGMENTIN (Trade Mark SmithKline Beecham). Because of this commercial interest, investigations into the understanding of clavam biosynthesis have concentrated on the biosynthesis of the 5R clavam, clavulanic acid, by *S. clavuligerus*. A number of enzymes and their genes associated with the biosynthesis of clavulanic acid have been identified and published. Examples of such publications include Hodgson, J. E. et al., Gene 166, 49-55 (1995), Aidoo, K. A. et al., Gene 147, 41-46 (1994), Paradkar, A. S. et al., J. Bact. 177(5), 1307-14 (1995). In contrast nothing is known about the biosynthesis and genetics of 5S clavams other than clavaminic acid which is a clavulanic acid precursor produced by the action of clavaminic acid synthase in the clavulanic acid biosynthetic pathway in *S. clavuligerus*.

Gene cloning experiments have identified that *S. clavuligerus* contains two clavaminic acid synthase isoenzymes, cas1 and cas2 [Marsh, E. N. et al Biochemistry 31, 12648-657, (1992)] both of which can contribute to clavulanic acid production under certain nutritional conditions [Paradkar, A. S. et al., J. Bact. 177(5), 1307-14 (1995)]. Clavaminic acid synthase activity has also been detected in other clavulanic acid producing micro-organisms, ie. *S. jumonjinensis* [Vidal, C. M., ES 550549, (1987)] and *S. katsurahamanus* [Kitano, K. et al., JP 53-104796, (1978)] as well as *S. antibioticos*, a producer of the 5S clavam, valclavam [Baldwin, J. E. et al., Tetrahedron Letts. 35(17), 2783-86, (1994)]. The latter paper also reported *S. antibioticos* to have proclavaminic acid amidino hydrolase activity, another enzyme known to be involved in clavulanic acid biosynthesis. All other genes identified in *S. clavuligerus* as involved in clavam biosynthesis have been reported to be required for clavulanic acid biosynthesis [Hodgson, J. E. et al., Gene 166, 49-55 (1995), Aidoo, K. A. et al., Gene 147, 41-46 (1994)] and as yet none have been reported which are specific for the biosynthesis of 5S clavams.

BRIEF SUMMARY OF THE INVENTION

The present invention relates to novel bacterial genes, processes for improving the manufacture of clavams, and novel organisms capable of producing increased amounts of clavulanic acid.

BRIEF DESCRIPTION OF THE DRAWINGS

FIG. 1 shows the nucleotide sequence of the *S. clavuligerus* chromosome including the flanking cas1 (SEQ ID NO. 1).

DETAILED DESCRIPTION OF THE INVENTION

By "gene" as used herein we also include any regulatory region required for gene function or expression. In a preferred aspect the DNA is as identified as FIG. 1. Preferably the DNA comprises the nucleotide sequences indicated in FIG. 1 designated as orfup3, orfup2, orfup1, orfdwn1, orfdwn2 and orfdwn3. The present invention also provides proteins coded by said DNA. The present invention also provides vectors comprising the DNA of the invention and hosts containing such vectors.

Surprisingly we have found that when at least one of the genes according to the invention is defective the amount of clavulanic acid produced by the organism is increased. Accordingly the present invention also provides processes for increasing the amount of clavulanic acid produced by a suitable microorganism. In one aspect of the invention the genes identified can be manipulated to produce an organism capable of producing increased amounts of clavam, suitably clavulanic acid. The findings of the present work also allow an improved process for the identification of organisms with higher clavulanic acid production comprising a preliminary screening for organisms with low or no 5S clavam production (for example by hplc and/or clavam bioassay as described in the examples herein).

Suitably the 5S clavam genes of the present invention can be obtained by conventional cloning methods (such as PCR) based on the sequences provided herein. The function of the gene can be interfered with or eliminated/deleted by genetic techniques such as gene disruption [Aidoo, K. A. et al., (1994), Gene, 147, 41-46], random mutagenesis, site directed mutagenesis and antisense RNA.

In a further aspect of the invention there are provided plasmids containing one or more defective genes, preferably the plasmids pCEC060, pCEC061, pCEC056 and pCEC057, described below.

Suitably, the plasmids of the invention are used to transform an organism such as S. clavuligerus, e.g. strain ATCC 27064 (which corresponds to S. clavuligerus NRRL 3585). Suitable transformation methods can be found in relevant sources including: Sambrook, J., Fritsch, E. F. and Maniatis, T. (1989), *Molecular cloning: a laboratory manual, 2nd Ed.*, Cold Spring Harbor Laboratory, Cold Spring Harbor, N.Y.; Hopwood, D. A. et al. (1985), *Genetic Manipulation of Streptomyces. A Cloning Manual*, and Paradkar, A. S. and Jensen, S. E. (1995), J. Bacteriol. 177 (5): 1307-1314.

Strains of the species S. clavuligerus are used industrially to produce clavulanic acid (potassium clavulanate). Within the British and United States Pharmacopoeias for potassium clavulanate (British Pharmacopoeia 1993, Addendum 1994, p1362-3 and U.S. Pharmacopeia Official Monographs 1995, USP 23 NF18 p384-5) the amounts of the toxic 5S clavam, clavam-2-carboxylate, are specifically controlled.

Therefore in a further aspect of the invention there is provided an organism capable of producing high amounts of clavulanic acid but has been made unable to make C2C or capable of producing high amounts of clavulanic acid but able to make only low levels of C2C. Suitably the clavulanic acid producing organism contains one or more defective clavam genes, and is preferably the S. clavuligerus strain 56-1A, 56-3A, 57-2B, 57-1C, 60-1A, 60-2A, 60-3A, 61-1A, 61-2A, 61-3A, and 61-4A, described below. Such organisms are suitable for the production of clavulanic acid without the production of the 5S clavam, clavam-2-carboxylate or with significantly reduced production of clavam-2-carboxylate.

EXAMPLES

In the examples all methods are as in Sambrook, J., Fritsch, E. F. and Maniatis, T. (1989) Molecular Cloning A Laboratory Manual (2nd Edition), or Hopwood, D. A. et al. (1985) Genetic Manipulation of *Streptomyces*. A Cloning Manual, and Paradkar, A. S. and Jensen, S. E. (1995) J. Bacteriol. 177 (5): 1307-1314 unless otherwise stated.

I. DNA Sequencing of the *Streptomyces clavuligerus* Chromosome Upstream and Downstream of the Clavaminate Synthase Gene cas1.

A. Isolation of cas1.

To isolate chromosomal DNA fragments from *Streptomyces clavuligerus* NRRL 3585 encoding the gene for clavaminate synthase isozyme 1 (cas1) an oligonucleotide probe RMO1 was synthesised based on nucleotides 9-44 of the previously sequenced cas1 gene (Marsh, E. N., Chang, M. D. T. and Townsend, C. A. (1992) Biochemistry 31: 12648-12657). Oligonucleotides were constructed using standard methods on an Applied Biosystems 391 DNA Synthesiser. The sequence of RMO1, a 36-mer, was synthesised in the antiparallel sense to that published by Marsh et al (1992, ibid) RMO1 was radiolabelled with $^{32}$P using standard techniques for end-labelling DNA oligonucleotides (Sambrook et al., 1989 ibid), and was used to screen a cosmid bank of *Streptomyces clavuligerus* genomic DNA by Southern hybridization as described by Stahl and Amann (In: Nucleic acid techniques in bacterial systematics. Ed. E. Stackebrandt and M. Goodfellow. Toronto: John Wiley and Sons, p. 205-248, 1991). The genomic bank of *S. clavuligerus* DNA, prepared in cosmid pLAFR3, was as described by Doran, J. L et al., (1990), J. Bacteriol. 172 (9), 4909-4918.

Colony blots of the *S. clavuligerus* cosmid bank were incubated overnight with radiolabelled RMO1 at 60° C. in a solution consisting of 5×SSC, 5×Denhardt's solution, and 0.5% SDS (1×SDS: 0.15 M NaCl+0.015 M Na$_3$citrate; 1×Denhardt's solution: 0.02% BSA, 0.02% Ficoll, and 0.02% PVP). The blots were then washed at 68° C. for 30 minutes in a solution of 0.5×SSC+0.1% SDS. One cosmid clone, 10D7, was isolated that hybridised strongly to RMO1 and gave hybridization signals upon digestion with restriction endonucleases SacI and EcoRI that were consistent with hybridization signals detected in similar experiments with digests of *S. clavuligerus* genomic DNA.

B. DNA Sequencing of the *S. clavuligerus* Chromosome Flanking cas1.

A partial restriction map of cosmid 10D7 was generated using restriction endonucleases SacI, NcoI, and KpnI. Southern hybridization experiments between RMO1 and various digests of 10D7 DNA indicated that cas1 was most likely located at one end of a 7-kb SacI-SacI DNA subfragment. This fragment consisted of the cas1 open reading frame and approximately 6 kb of upstream DNA. The 7-kb fragment was then subcloned from a SacI digest of 10D7 in the phagemid vector pBluescriptII SK+ (2.96 kb; Stratagene), thus generating the recombinant plasmid pCEC007.

To facilitate the process of sequencing the chromosome upstream of cas1, a 3-kb NcoI-NcoI subfragment of the 7-kb SacI-SacI fragment was subcloned in pUC120 (3.2 kb; Vieirra and Messing, Methods Enzymol. 153, 3-11, 1987)) in both orientations, generating the recombinant plasmids pCEC026 and pCEC027. The 3-kb subfragment consisted of the amino-terminal-encoding portion of cas1 and approximately 2.6 kb of upstream DNA.

Nested, overlapping deletions were created in both pCEC026 and pCEC027 using exonuclease III and S1 nuclease digestion (Sambrook et al., 1989 ibid) and the DNA sequence of the 3-kb NcoI-NcoI fragment was determined on both strands by the dideoxy chain termination method (Sanger, F., Nicklen, S. and Coulson, A. R. (1977), Proc. Natl. Acad. Sci. U.S.A. 74: 5463-5467) using a Taq dye-deoxy$^a$ terminator kit and an Applied Biosystems 373A Sequencer.

To determine the DNA sequence of the chromosome immediately downstream of cas1 a 4.3-kb KpnI-EcoRI DNA fragment was subcloned from cosmid clone 10D7 in pBluescriptII SK+, generating pCEC018. From pCEC018 a 3.7-kb SacI-SacI subfragment was cloned in pSL1180 (3.422 kb, Pharmacia); one of the SacI termini of this fragment partially overlapped the TGA stop codon of cas1, the other was vector encoded. Both orientations of the 3.7-kb fragment were obtained during subcloning and the resulting recombinant plasmids were designated pCEC023 and pCEC024. Nested, overlapping deletions were created in both plasmids and the DNA sequence of the 3.7-kb fragment was determined on both strands. The nucleotide sequence of the *S. clavuligerus* chromosome generated in these experiments, including and flanking cas1 sequence is shown in FIG. 1.

II. Functional Analysis of the Open Reading Frames Flanking cas1.

Computer analysis of the DNA sequence upstream of cas1 predicted the presence of two complete orfs and one incomplete orf. All three orfs were located on the opposite DNA strand to cas1 and were thus oriented in the opposite direction. The first open reading frame, orfup1, was located 579 bp upstream of cas1 and encoded a polypeptide of 344 amino acids (aa). The second open reading frame, or p2, was located at 437 bp beyond the 3'-end of orfup1 and encoded a 151 aa polypeptide. Beyond orfup2 is orfup3. The start codon of orfup3 overlaps the translational stop codon of orfup2, suggesting that the two orfs are translationally coupled. No translational stop codon for orfup3 was located on the 3-kb NcoI-NcoI fragment.

A similar analysis of the DNA sequence downstream of cas1 predicted the presence of two complete orfs and one incomplete orf. Two of the orfs were located on the opposite DNA strand to cas1 and were thus oriented towards cas1. The third orf was located on the same strand as cas1 and was thus oriented away from it. The first downstream open reading frame, orfdwn1, was located 373 bp downstream of cas1 and encoded a 328 aa polypeptide. The second open reading frame, orfdwn2, was located 55 bp upstream of orfdwn1 and encoded a 394 aa polypeptide. At 315 bp upstream of orfdwn2 and on the opposite strand was orfdwn3. Because no stop codon was observed for orfdwn3 on the 3.7-kb fragment, it encoded an incomplete polypeptide of 219 aa.

Gene Disruption of the orfup and orfdwn Open Reading Frames

To assess the possible roles of the open reading frames flanking cas1 in the biosynthesis of clavulanic acid and the other clavams produced by *S. clavuligerus*, insertional inactivation or deletion mutants were created by gene replacement. The method used for gene disruption and replacement was essentially as described by Paradkar and Jensen (1995 ibid).

A. orfup1

A 1.5-kb NcoI-NcoI fragment carrying the apramycin resistance gene (apr$^r$), constructed as described in Paradkar and Jensen (1995 ibid), was treated with Klenow fragment to generate blunted termini (Sambrook et al., 1989 ibid) and was ligated to pCEC026 that had been digested with BsaBI and likewise treated with Klenow fragment. pCEC026 possesses a BsaBI site located within orfup1 at 636 bp from the translational start codon. The ligation mixture was used to transform competent cells of *E. coli* GM 2163 (available from New England Biolabs, USA., Marinus, M. G. et al M G G (1983) vol 122, p288-9) to apramycin resistance. From the resulting transformants two clones containing plasmids pCEC054 and pCEC055 were isolated; by restriction analysis pCEC054 was found to possess the apr$^r$-fragment inserted in the same orientation as orfup1, while pCEC055 possessed it in the opposite orientation.

To introduce pCEC054 into *S. clavuligerus*, plasmid DNA was digested with BamHI and HindIII and ligated to the high-copy number *Streptomyces* vector pIJ486 (6.2 kb; Ward et al., (1986) Mol. Gen. Genet. 203: 468-478). The ligation mixture was then used to transform *E. coli* GM2163 competent cells to apramycin resistance. From the resulting transformants one clone, possessing the shuttle plasmid pCEC061, was isolated. This plasmid was then used to transform *S. clavuligerus* NRRL 3585. The resulting transformants were put through two successive rounds of sporulation on non-selective media and then replica plated to antibiotic containing media to identify apramycin-resistant and thiostrepton-sensitive transformants. From this process four putative mutants (61-1A, -2A, -3A and -4A) were chosen for further analysis.

To confirm that these putative mutants were disrupted in orfup1 genomic DNA was prepared from isolates 61-1A and 61-2A, digested with SacI and subjected to Southern blot analysis. The results of the Southern blot were consistent with a double cross-over having occurred and demonstrated that these mutants are true disruption replacement mutants in orfup1.

The mutants 61-1A, -2A, -3A and -4A were grown in Soya-Flour medium and their culture supernatants were assayed by HPLC for clavulanic acid and clavam production. The composition of the Soya-Flour medium and the method for assaying clavams by HPLC were as previously reported (Paradkar and Jensen, 1995 ibid) except that the running buffer for the HPLC assay consisted of 0.1 M NaH$_2$PO$_4$+6% methanol, pH 3.68 (adjusted with glacial acetic acid). The HPLC analysis indicated that none of the mutants produced detectable levels of clavam-2-carboxylate or 2-hydroxymethylclavam. Furthermore, when culture supernatants were bioassayed against *Bacillus* sp. ATCC 27860, using the method of Pruess and Kellett (1983, J. Antibiot. 36: 208-212), none of the mutants produced detectable levels of alanylclavam. In contrast, HPLC assays of the culture supernatants showed that the mutants appeared to produce superior levels of clavulanic acid when compared to the wild-type (Table 1).

TABLE 1

Clavulanic acid titre (CA) of orfup1 mutants in shake flask tests

| STRAIN | 70 HOURS CA ug/ml | 70 HOURS CA ug/mg DNA | 93 HOURS CA ug/ml | 93 HOURS CA ug/mg DNA |
| --- | --- | --- | --- | --- |
| NRRL 3585 #1 | 87 | 915 | 166 | 1963 |
| NRRL 3585 #2 | 66 | 790 | 159 | 1842 |
| 61-1A | 272 | 2894 | 439 | 6113 |
| 61-2A | 199 | 2148 | 225 | 2928 |
| 61-3A | 54 | 692 | 221 | 2585 |
| 61-4A | 0 | 0 | 226 | 2422 |

B. orfdwn1 and orfdwn2

A deletion/replacement mutant in orfdwn1 and orfdwn2 was created by first digesting pCEC018 (7.3 kb) with NcoI and liberating a 1-kb subfragment containing most of orfdwn1 and a portion of orfdwn2. The digest was fractionated by agarose-gel electrophoresis and the 6.3-kb fragment was excised and eluted from the gel. This fragment was then ligated to an NcoI-NcoI DNA fragment carrying apr$^r$ and used to transform *E. coli* XL1-Blue to apramycin resistance. One clone was obtained from this experiment but restriction analysis of the resulting recombinant plasmid revealed that two copies of the apramycin resistance fragment had been ligated into the deletion plasmid. To eliminate the extra copy of the apr$^r$-fragment, the plasmid was digested with NcoI and self-ligated. The ligation mixture was used to transform *E. coli* GM2163 to apramycin resistance. From the transformants, two clones were isolated that contained plasmids pCEC052 and pCEC053 both of which possessed only one copy of the apr$^r$-fragment; pCEC052 possessed the apr$^r$-fragment inversely oriented with respect to orfdwn1 and 2, while pCEC053 possessed the apr$^r$-fragment inserted in the same orientation as orfdwn1 and 2.

A shuttle plasmid of pCEC052 was constructed by ligating BamHI-digested pCEC052 with similarly digested pIJ486 and transforming *E. coli* GM2163 to apramycin resistance. From this experiment one clone was isolated that contained the shuttle plasmid pCEC060. This plasmid was used to transform wild-type *S. clavuligerus* 3585 to apramycin and thiostrepton resistance. The resulting transformants were put through two rounds of sporulation under non-selective conditions and then replica plated to antibiotic containing media to identify apramycin resistant, thiostrepton sensitive colonies. Three putative mutants (60-1A, -2A and -3A) were chosen for further analysis.

To establish the identity of these putative mutants genomic DNA was isolated from strains 60-1A and 60-2A and digested with either SacI or BstEII and subjected to southern blot analysis. The hybridisation bands generated from this experiment were consistent with both strains having undergone a double cross-over event demonstrating that these mutants are true disruption replacement mutants in orfdwn1/2.

When these were cultured in Soya-Flour medium and their culture supernatants assayed by HPLC, none of the mutants produced detectable levels of clavam-2-carboxylate or 2-hydroxymethylclavam. A bioassay of the culture supernatants showed that the mutants also failed to produce detectable levels of alanylclavam. As with the orfup1 mutants, the orfdwn1/2 mutants are capable of producing superior to wild-type levels of clavulanic acid (Table 2).

TABLE 2

Clavulanic acid titre (CA) of orfdwn1/2 mutants in shake flask tests

| STRAIN | 70 HOURS CA ug/ml | 70 HOURS CA ug/mg DNA | 93 HOURS CA ug/ml | 93 HOURS CA ug/mg DNA |
| --- | --- | --- | --- | --- |
| NRRL 3585 #1 | 87 | 915 | 166 | 1963 |
| NRRL 3585 #2 | 66 | 790 | 159 | 1842 |
| 60-1A | 164 | 1872 | 260 | 2911 |
| 60-2A | 187 | 2013 | 108 | 1320 |
| 60-3A | 79 | 994 | 214 | 2161 | orfdwn3

To disrupt orfdwn3 pCEC023 (consisting of a 3.7-kb fragment of cas1 downstream DNA subcloned into pSL1180) was digested with NcoI and then self ligated. After transforming *E. coli* with the ligation mixture a clone was isolated that possessed the plasmid pCEC031. This plasmid retained only the 1.9 kb NcoI-EcoRI fragment encoding a portion of orfdwn2 and the incomplete orfdwn3. An examination of the DNA sequence revealed that pCEC031 possessed a unique BstEII site at 158 bp from the translational start site of orfdwn3. Therefore, pCEC031 was digested with BstEII, treated with Klenow fragment to create blunt ends and then ligated to a blunted apramycin resistance cassette. The ligation mixture was used to transform *E. coli* GM2163 to apramycin resistance and ampicillin resistance. Two transformants were selected that contained respectively pCEC050 and pCEC051. restriction analysis revealed that the apramycin resistance cassette was orientated in the same orientation as orfdwn3 in pCEC050 and in the opposite orientation in pCEC051. Both of these plasmids were then digested with HindIII and ligated to similarly digested pU486. The ligation mixtures were then used separately to transform *E. coli* GM2163 to apramycin and ampicillin resistance. The shuttle plasmids pCEC056 (pCEC050+pU486) and pCEC057 (pCEC051+pIJ486) were isolated from the resultant transformants. Both plasmids were then used to transform *S. clavuligerus* NRRL 3585.

One transformant was selected from each transformant experiment and put through two successive rounds of sporulation on non-selective media and then replica plated to antibiotic containing media to identify apramycin-resistant and thiostrepton-sensitive transformants. From this process two putative mutants were isolated from the progeny of each primary transformant. (56-1A and 56-3A for pCEC056, and 57-1C and 57-2B for pCEC057).

To establish the identity of these putative mutants genomic DNA was isolated from these strains and digested with either SacI or Acc65I and subjected to Southern blot analysis. The hybridisation bands generated from this experiment were consistent with both strains having undergone a double cross-over event demonstrating that these mutants are true disruption replacement mutants in orfdwn3.

When these strains were cultured in Soya-Flour medium and their culture supernatants assayed by HPLC, the mutants produced greatly reduced levels of clavam-2-carboxylate or 2-hydroxymethylclavam. A bioassay of the culture supernatants showed that the mutants also failed to produce detectable levels of alanylclavam. As with the orfup1 and orfdwn1/2 mutants, the orfdwn3 mutants were capable of producing superior to wild-type levels of clavulanic acid (Table 3).

TABLE 3

Clavulanic acid titre (CA) of orfdwn3 mutants in shake flask tests

| STRAIN | 71 HOURS CA ug/ml | 71 HOURS CA ug/mg DNA | 93 HOURS CA ug/ml | 93 HOURS CA ug/mg DNA |
| --- | --- | --- | --- | --- |
| NRRL 3585 #1A | 180 | 1580 | 193 | 1790 |
| NRRL 3585 #1B | 179 | 1640 | 266 | 2310 |
| 56-1A | 34 | 110 | 235 | 2160 |
| 56-3A | 225 | 2140 | 274 | 2740 |
| 57-1C | 253 | 2910 | 277 | 2920 |
| 57-2B | 242 | 2240 | 193 | 1860 |

The application discloses the following nucleotide sequences:

SEQ ID No. 1: DNA sequence of FIG. 1

SEQ ID No. 2: orfup3 sequence

SEQ ID No. 3: orfup2 sequence

SEQ ID No. 4: orfup1 sequence

SEQ ID No. 5: orfdwn1 sequence

SEQ ID No. 6: ofrdwn2 sequence

SEQ ID No. 7: orfdwn3 sequence

SEQUENCE LISTING

<160> NUMBER OF SEQ ID NOS: 19

<210> SEQ ID NO 1

```
<211> LENGTH: 7193
<212> TYPE: DNA
<213> ORGANISM: Streptomyces clavuligerus

<400> SEQUENCE: 1
ccatggcggg cggcggctgc cccggagcct cggccggacc ggtgaccagg accaccccgg      60
tgggatagtg gccgccacc cggcgcagca gactcccgga cacggacccg tgggtgtgcg     120
cggaaaggcc cggaggccgg gtcacagcca cgggtaacgc gcggtgtcct tgcccgcgta    180
atcggggtcc agatagacga aggcccggtg gacgaggaag tcccgcacct cgtagaccgt    240
gcaccagcgc ccggcggccc actcggggtc acccgcccgc cacggcccgt cccggtgctc    300
accgtgggtg gtgccctccg cggcgaggag ttcggtcccg gtcagaatcc agttgacgga    360
ccacagatgt tgggtgatcg agcggatggt gcccccgagg tcgtcgaaga gccgggcgat    420
ctcggacttg ccccgggcca gaccccactt ggggaagaag aagaccgcgt cctcggcgaa    480
gtagtcgatc gcggggtgc cgtcgctgcc gacgccgccg ttgtcgaacg ccttgaagta    540
cgcggtgatg accgccttgc gctgctcgtc cgtcataccg gccgatgcca cggacatgaa    600
acgacctcca gagattccgg gtggctgtgc tggggctgcg gaaggggtgt ccccgcgaa    660 ggacggcgga cgccgcggac gccgcggccg tctccccggc ggacgggtcc cagcgtcctg    720
gagagggctt ggcggcggct tgacgccgtg ctgtcccgcg gcttgcggaa cgcgaagtac    780
cggccagcgt acgggcgttg caccggacgt gtacgccggt cgggacccct cgtaccccg    840 gagccggccg accccggcgg ctccgggggt acggacgcgc cggaccggcc cgagcgagcc    900
ggacgggtcg gacggtgcgc gtggttccgg tgtgtcggac agctcggacg gaccggacgg    960
tgcgcgtggt tccggtgtgt cggacagctc ggacgggtcg gacggtgcgc gtggttccgg   1020
cacgccggac gggtcagttg ccgatcatgg cgagcaatgc cggggtgtac cgctccccgg   1080
acaccgggtg ggagatcgcg gccgtcacct ccgcgaggga ccgtcgtcc agccggatcg   1140 aggcggcggc gagattgtcc gcgagatggg ccgggttcgc ggtgcccggg atcgggacga   1200
cgtcctcgcc ccggtggtgc agccaggcga gcgcgagctg tgccagggtc agccccagac   1260
cgtccgcgac cgggcgcagc cggtgcagca acgagcggtt gcgcgcgagg gccggagcgc   1320
tgaaccgggg ctggccccgg cggaagtcct cgtcccccag atcgtcggtg gtgcggatgg   1380
tgccggtgag aaaaccccgt cccagagggg cgtaagcgac gatcccgatc ccagctcccc   1440
ggcagacggg caccacctcg tcctcgatcc cgcgcgacca caggctccac tcgctctgca   1500
ccgccgtcac cgggtgcacc gcgtccgccc ggcgcagcgt ggccgcggag ggctcggaga   1560
gaccgagcct gcggaccttg ccctcgcgca ccagctcggc caccgcaccc acggtctcct   1620
cgatcggcac cgccgggtcc gtccagtgct ggtagtacga gtcgatgcgg tcggtgccga   1680
gacgacgcag ggaccgttcg caggccgcgc ggacgtagga cggctcgccg cacaagccct   1740
gggaggcgcc gtcggacgag cgcaccatgc cgaacttggt ggcgatcagc acctcgtccc   1800
ggcggcccgc gaccgcccgt ccgagcagct cctcaccggc gccgagcccc tggacgtcgg   1860
cggtgtccag cagggtgacc ccggcgtcga cggcggcgcg gatggtggcc gtcgcccggg   1920
cgcggtccgg gcgtccgtag aagtcggtgg tcggcaggca gccgagcccc tgggcactga   1980
ccggaaggtc ccgcagggcg cggaccggcg gacgcgaaac cgcggcggac acggaaccgg   2040
ccggggactc gggcggagag cgggacatac ggaacctcca caggcggagc cgggaacggg   2100
acgagggcga ggacgggacg gaacgaagga gaggacggga cggacagcac ggacgggacg   2160
gacggaacgg agtcgggaac cgggggggggt gaccggaacc gggccgtcct tggccctccc   2220
```

```
ccgtcctccc cgccatccgc cgttctcccc cgttccctct cccgtcctcc agccaacacc   2280
gccgcccttt ccaagcgctt gacacggcac cgacagccgc cgccgggcgc ccgatgggga   2340
cccgtgcccg ccggtgagcg gcggtgagcg ccggtacggg accccacgcg ccgccgcccg   2400
ggcgcccgcc agggcccgcg cggccacccc ggcccgcccc ggccggagcg gcgatccggg   2460
ccgctcgctg caagaggaac atccacagcc gcacaaggag cgctccgcac agtgggcacc   2520
acgtccgccc cgtcccccac accgtggccg gtccccaccg gacagcacag caccgcacag   2580
caccacatcg cacggcacag cacagcacca ccggcacgag gaaccaagga aaggaaccac   2640
accaccatga cctcagtgga ctgcaccgcg tacggccccg agctgcgcgc gctcgccgcc   2700
cggctgcccc ggaccccccg ggccgacctg tacgccttcc tggacgccgc gcacacagcc   2760
gccgcctcgc tccccggcgc cctcgccacc gcgctggaca ccttcaacgc cgagggcagc   2820
gaggacggcc atctgctgct gcgcggcctc ccggtggagg ccgacgccga cctccccacc   2880
accccgagca gcacccccgg cgccgaggac cgctccctgc tgaccatgga ggccatgctc   2940
ggactggtgg gccgccggct cggtctgcac acggggtacc gggagctgcg ctcgggcacg   3000
gtctaccacg acgtgtaccc gtcgcccggc gcgcaccacc tgtcctcgga gacctccgag   3060
acgctgctgg agttccacac ggagatggcc taccaccggc tccagccgaa ctacgtcatg   3120
ctggcctgct cccgggccga ccacgagcgc acggcggcca cactcgtcgc ctcggtccgc   3180
aaggcgctgc ccctgctgga cgagaggacc cgggcccggc cctcgaccg gaggatgccc   3240
tgctgcgtgg atgtggcctt ccgcggcggg gtggacgacc cggcgccat cgcccaggtc   3300
aaaccgctct acggggacgc ggacgatccc ttcctcgggt acgaccgcga gctgctggcg   3360
ccggaggacc ccgcggacaa ggaggccgtc gccgccctgt ccaaggcgct cgacgaggtc   3420
acggaggcgg tgtatctgga gcccggcgat ctgctgatcg tcgacaactt ccgcaccacg   3480
cacgcgcgga cgccgttctc gccccgctgg gacgggaagg accgctggct gcaccgcgtc   3540
tacatccgca ccgaccgcaa tggacagctc tccggcggcg agcgcgcggg cgacgtcgtc   3600
gccttcacac cgcgcggctg agctcccggg tccgacaccg cgcggctgaa cccacggtcc   3660
ggggcccacg gtccggcacc gcgcggctga gcccccgggt ccggcagcgg gcggctgaac   3720
ccccgccccg ggccaccgcc cgaccgcccc gcgcaccgg acgcgccgc ctgtacggcg   3780
gtcccgcccg ggcccgtaca cctgaagcgc ccggcggacc gccgccccgc cggggacgg   3840
acagagccgg gtgcgggagg acgtcctccc gcacccggct cccaccgttc cgcaccgacc   3900
gcacccgacc gtgccgcagg cgccaccggc accgcaccgc ccgcgccggc agccaccaca   3960
ggcgccacgc cgcccgcacg gtgccgcgcg tgctcagccc ccgtccaccg ggctgtccag   4020
cagccgccgc agcgcgcccc cgatgaactc ccggtcggcg gccgaccccc cggacccgc   4080
gagatgcccc cacactcccg ggatcacctc cagcgaggca tacggcagca gatcggccac   4140
ccgcttctcg tcctcgacgg cgaaacacac gtccagggcg cccggcagca ccacggcccg   4200
cgccgtgacg gaggccagcg ccgcctcgac gctccccccg gccccgggtg tcgccccac   4260
atccgtgttc tcccaggtgc gcaccatggt gagcagatcc gcggcgccgg gcccggagag   4320
gaagacctgc tcccagaagc cggtgaggta ctcctcgcgg gtggcgaaac ccagctcccg   4380
gtgggcacgg cgggcccaga aggaacgcga ggtccccac ccggcgaaca cccggcccgc   4440
cgccttccgc ccccgctccc cggcgtcggc gctgagcgcc gcggcagac cggacagcag   4500
gaccaggctg tgcgggctgc tcaccggcgc cccgcagatc ggggcgatcc ggcgcaccat   4560
```

```
ccccggatgc gacacggccc actggtaggc gtgggccgcg cccatcgacc agcccgtgac   4620
cagggccagt tcccgtaccc ccagctcctc ggtgagcagc cggtgctgcg ccgcgacatt   4680
gtcctgcgga gtgatcagcg gaaagcggga ccccgacggg tggttgccgg gcgagctgga   4740
gaccccgttg ccgaagagtc cggcggtgac gacgcagtac cgccgggtgt ccagcggcag   4800
ccccgcaccg atcagccagt cgtacccggt gtggtcccgg ccgaagaacg acggacagag   4860
caccacgttc gtcccgtcgg cgttcggcgt gccgtacatg gcgtaaccga tccgggcgtc   4920
ccgcaggacc tccccgtcca gcaacggcag ttcgtcgatc tcgaatatgc ggcattccac   4980
cgctgacctc cttgttcgat cccccggac aacaggtcgg tcgtggccgg agactcgagg    5040
ccagttgggg gcgatctcgg tggcccacag ctccaggctg cgcagctgga catcgtgcgg   5100
gatcagcccg gagtactggc actggagcag atactccgga tcgtgccgct ccaccagctt   5160
ctcgatcatg cggttgatgt cgtccggggt gccgacccac tccagccccc ggtcgaccag   5220
ggtcttgtag tccgagccga tcggaccccgt ctcgccggtc gcgcgcagcg cctcggtgaa  5280
gcccatgggg ccgaaccagt tctcgaagat gaagccgccg ccgcgggacg cccagtggtg   5340
ggcctcgccg gagtcccggg agaccaggac gtccttcatc accccgaccc gctcgccccg   5400
ccgcagggtg ccgtggcccg ccgcctcggc ctcctcccgg tagatgtcca tcagccgggc   5460
gacgatctgg tcgtcggtgt tcatcaggat cggcaccacg ccctcccggg cacagaaccg   5520
gaacgtgtcc tcactgaagc tgaacggctg gaagacgggc gggtgggggc gctggtaggg   5580
cttgggcgcg atgcccacct cgcggatgac gccgttctcg tcgaggcccc ggccgtagcg   5640
gcgcaccgcc tcgtagggga actccaggtc cggcaccggg atcgtccact gctccccgga   5700
gtgggtgaac gtctccggtcg tccacgcctt cttgatgatc tcccagtgct cctcgaagag   5760
ggcacgattg cgccggtccc gctccccggc gtcggacagg gtgccgccga ccccgtacac   5820
ctgccccatg atgtcggccc agcgcttctg gaacccgcgc gcgatcccga cgaaggcgcg   5880
gccccgggtc atgtggtcga gcatcgccag atcctcggcc agccgcagcg gattgtgcag   5940
cggcaggacg ttggccatct ggccgacccg gatgtgccgg gtctgcatgc cgaggtagag   6000
ccccagcatg atcgggttgt tggagacctc gaaaccctcg gtgtggaagt ggtgctcggt   6060
gaaggacagt ccccagtagc cgagttcgtc ggccgcctgc gcctgccggg tgagctgccg   6120
gagcatgttc tggtagttct gcggattgac ccccgccata ccccgctgga cctgcgcatg   6180
actgccgacc gttggcagat agaagagaat ggacttcacc ctggctcctc cggttcgcgg   6240
cgccctccat tgacgtgcgc cgaaagcggc tcgaccgtcc cactccgccc ttgagttccg   6300
tctgacgccg cgccagtcgg cgggccgtcc gccggggtgc cgccggggt ccgcacccgc    6360 cggacggcac ggcgcgcacc gcgcgcgcgg cgcttcgggg caccgggctc gacggggtgc   6420
tcagcgggac gtccaacgga aggcaagccc ccgtacccag cctggtcaag gcgctcatcg   6480
ccattccctg aggaggtccc gccttgacca cagcaatctc cgcgctcccg accgtgcccg   6540
gctccggact cgaagcactg gaccgtgcca ccctcatcca ccccacccctc tccggaaaca   6600 ccgcggaacg gatcgtgctg acctcggggt ccggcagccg gtccgcgac accgacggcc    6660 gggagtacct ggacgcgagc gccgtcctcg gggtgaccca ggtgggccac ggccgggccg   6720
agctggcccg ggtcgcggcc gagcagatgg cccggctgga gtacttccac acctggggga   6780
cgatcagcaa cgaccgggcg gtggagctgg cggcacggct ggtggggctg agcccggagc   6840
cgctgacccg cgtctacttc accagcgcgc gggccgaggg caacgagatc gccctgcgga   6900
tggcccggct ctaccaccac cggcgcgggg agtccgcccg tacctggata ctctcccgcc   6960
```

```
ggtcggccta ccacggcgtc ggatacggca gcggcggcgt caccggcttc cccgcctacc    7020
accagggctt cggcccctcc ctcccggacg tcgacttcct gaccccgccg cagccctacc    7080
gccgggagct gttcgccggt tccgacgtca ccgacttctg cctcgccgaa ctgcgcgaga    7140
ccatcgaccg gatcggcccg gagcggatcg cggcgatgat cggcgagccg atc           7193

<210> SEQ ID NO 2
<211> LENGTH: 145
<212> TYPE: DNA
<213> ORGANISM: Streptomyces clavuligerus

<400> SEQUENCE: 2
gtgacccggc ctccgggcct ttccgcgcac acccacgggt ccgtgtccgg gagtctgctg      60
cgccgggtgg cgggccacta tcccaccggg gtggtcctgg tcaccggtcc ggccgaggct    120
ccggggcagc cgccgcccgc catgg                                          145

<210> SEQ ID NO 3
<211> LENGTH: 453
<212> TYPE: DNA
<213> ORGANISM: Streptomyces clavuligerus

<400> SEQUENCE: 3
atgtccgtgg catcggccgg tatgacggac gagcagcgca aggcggtcat caccgcgtac      60
ttcaaggcgt tcgacaacgg cggcgtcggc agcgacggca cccccgcgat cgactacttc    120
gccgaggacg cggtcttctt cttccccaag tggggtctgg cccggggcaa gtccgagatc    180
gcccggctct tcgacgacct cgggggcacc atccgctcga tcacccacca tctgtggtcc    240
gtcaactgga ttctgaccgg gaccgaactc ctcgccgcgg agggcaccac ccacggtgag    300
caccgggacg ggccgtggcg ggcgggtgac cccgagtggg ccgccgggcg ctggtgcacg    360
gtctacgagt gcgggacttt cctcgtccac cgggccttcg tctatctgga ccccgattac    420
gcgggcaagg acaccgcgcg ttacccgtgg ctg                                 453

<210> SEQ ID NO 4
<211> LENGTH: 1032
<212> TYPE: DNA
<213> ORGANISM: Streptomyces clavuligerus

<400> SEQUENCE: 4
atgtcccgct ctccgcccga gtccccggcc ggttccgtgt ccgccgcggt tccgcgtccg      60
ccggtccgcg ccctgcggga ccttccggtc agtgcccagg ggctcggctg cctgccgacc    120
accgacttct acggacgccc ggaccgcgcc cgggcgacgg ccaccatccg cgccgccgtc    180
gacgccgggg tcaccctgct ggacaccgcc gacgtccagg ggctcggcgc cggtgaggag    240
ctgctcggac gggcggtcgc gggccgccgg gacgaggtgc tgatcgccac caagttcggc    300
atggtgcgct cgtccgacgg cgcctcccag ggcttgtgcg gcgagccgtc ctacgtccgc    360
gcggcctgcg aacggtccct gcgtcgtctc ggcaccgacc gcatcgacct gtactaccag    420
cactggacgg acccggcggt gccgatcgag gagaccgtgg gtgcggtggc cgagctggtg    480
cgcgagggca aggtccgcag gctcggtctc tccgagccct ccgcggccac gctgcgccgg    540
gcggacgcgg tgcacccggt gacggcggtg cagagcgagt ggagcctgtg gtcgcgcggg    600
atcgaggacg aggtggtgcc cgtctgccgg gagctgggga tcgggatcgt cgcttacgcc    660
cctctgggac ggggttttct caccggcacc atccgcacca ccgacgatct gggggacgag    720
```

-continued

| | |
|---|---|
| gacttccgcc ggggccagcc ccggttcagc gctccggccc tcgcgcgcaa ccgctcgttg | 780 |
| ctgcaccggc tgcgcccggt cgcggacggt ctggggctga ccctggcaca gctcgcgctc | 840 |
| gcctggctgc accaccgggg cgaggacgtc gtcccgatcc cgggcaccgc gaacccggcc | 900 |
| catctcgcgg acaatctcgc cgccgcctcg atccggctgg acgaccggtc cctcgcggag | 960 |
| gtgacggccg cgatctccca cccggtgtcc ggggagcggt acaccccggc attgctcgcc | 1020 |
| atgatcggca ac | 1032 |

<210> SEQ ID NO 5
<211> LENGTH: 984
<212> TYPE: DNA
<213> ORGANISM: Streptomyces clavuligerus

<400> SEQUENCE: 5

| | |
|---|---|
| gtggaatgcc gcatattcga gatcgacgaa ctgccgttgc tggacgggga ggtcctgcgg | 60 |
| gacgcccgga tcggttacgc catgtacggc acgccgaacg ccgacgggac gaacgtggtg | 120 |
| ctctgtccgt cgttcttcgg ccgggaccac accgggtacg actggctgat cggtgcgggg | 180 |
| ctgccgctgg acaccggcg gtactgcgtc gtcaccgccg gactcttcgg caacggggtc | 240 |
| tccagctcgc ccggcaacca cccgtcgggg tcccgctttc cgctgatcac tccgcaggac | 300 |
| aatgtcgcgg cgcagcaccg gctgctcacc gaggagctgg gggtacggga actgccctg | 360 |
| gtcacgggct ggtcgatggg cgcggcccac gcctaccagt gggccgtgtc gcatccgggg | 420 |
| atggtgcgcc ggatcgcccc gatctgcggg gcgccggtga gcagcccgca cagcctggtc | 480 |
| ctgctgtccg gtctggccgc ggcgctcagc gccgacgccg gggagcgggg gcggaaggcg | 540 |
| gcgggccggg tgttcgccgg gtgggggacc tcgcgttcct tctgggcccg ccgtgcccac | 600 |
| cgggagctgg gtttcgccac ccgcgaggag tacctcaccg gcttctggga gcaggtcttc | 660 |
| ctctccgggc ccggcgccgc ggatctgctc accatggtgc gcacctggga gaacacggat | 720 |
| gtgggggcga caccggggc cggggggagc gtcgaggcgg cgctggcctc cgtcacggcg | 780 |
| cgggccgtgg tgctgccggg cgccctggac gtgtgtttcg ccgtcgagga cgagaagcgg | 840 |
| gtggccgatc tgctgccgta tgcctcgctg gaggtgatcc cgggagtgtg ggggcatctc | 900 |
| gcggggtccg gggggtcggc cgccgaccgg gagttcatcg ggggcgcgct gcggcggctg | 960 |
| ctggacagcc cggtggacgg gggc | 984 |

<210> SEQ ID NO 6
<211> LENGTH: 1182
<212> TYPE: DNA
<213> ORGANISM: Streptomyces clavuligerus

<400> SEQUENCE: 6

| | |
|---|---|
| gtgaagtcca ttctcttcta tctgccaacg gtcggcagtc atgcgcaggt ccagcggggt | 60 |
| atggcggggg tcaatccgca gaactaccag aacatgctcc ggcagctcac ccggcaggcg | 120 |
| caggcggccg acgaactcgg ctactgggga ctgtccttca ccgagcacca cttccacacc | 180 |
| gagggtttcg aggtctccaa caacccgatc atgctgggc tctacctcgg catgcagacc | 240 |
| cggcacatcc gggtcggcca gatggccaac gtcctgccgc tgcacaatcc gctgcggctg | 300 |
| gccgaggatc tggcgatgct cgaccacatg acccggggcc gcgccttcgt cgggatcgcg | 360 |
| cgcgggttcc agaagcgctg ggccgacatc atggggcagg tgtacgggt cggcggcacc | 420 |
| ctgtccgacg ccggggagcg ggaccggcgc aatcgtgccc tcttcgagga gcactgggag | 480 |
| atcatcaaga aggcgtggac gaccgagacg ttcacccact ccggggagca gtggacgatc | 540 |

-continued

```
ccggtgccgg acctggagtt ccCctacgag gcggtgcgcc gctacggccg gggcctcgac      600
gagaacggcg tcatccgcga ggtgggcatc gcgcccaagc cctaccagcg ccccaccccg      660
cccgtcttcc agccgttcag cttcagtgag gacacgttcc ggttctgtgc ccggagggc       720 gtggtgccga tcctgatgaa caccgacgac cagatcgtcg cccggctgat ggacatctac      780
cgggaggagg ccgaggcggc gggccacggc accctgcggc ggggcgagcg ggtcggggtg      840
atgaaggacg tcctggtctc ccgggactcc ggcgaggccc accactgggc gtcccgcggc      900
ggcggcttca tcttcgagaa ctggttcggc cccatgggct tcaccgaggc gctgcgcgcg      960
accggcgaga cgggtccgat cggctcggac tacaagaccc tggtcgaccg ggggctggag    1020
tgggtcggca ccccgacgac catcaaccgc atgatcgaga gctggtggac gcggcacgat    1080
ccggagtatc tgctccagtg ccagtactcc gggctgatcc cgcacgatgt ccagctgcgc    1140
agcctggagc tgtgggccac cgagatcgcc cccaactggc tc                        1182
```

<210> SEQ ID NO 7
<211> LENGTH: 660
<212> TYPE: DNA
<213> ORGANISM: Streptomyces clavuligerus

<400> SEQUENCE: 7

```
gtgcccggct ccggactcga agcactggac cgtgccaccc tcatccaccc caccctctcc       60
ggaaacaccg cggaacggat cgtgctgacc tcggggtccg gcagccgggt ccgcgacacc      120
gacgccgggg agtacctgga cgcgagcgcc gtcctcgggg tgacccaggt gggccacggc      180
cgggccgagc tggcccgggt cgcggccgag cagatggccc ggctggagta cttccacacc      240
tgggggacga tcagcaacga ccgggcggtg gagctggcgg cacggctggt ggggctgagc      300
ccggagccgc tgacccgcgt ctacttcacc agcggcgggg ccgagggcaa cgagatcgcc      360
ctgcggatgg cccggctcta ccaccaccgg cgcggggagt ccgcccgtac ctggatactc      420
tcccgccggt cggcctacca cggcgtcgga tacggcagcg gcggcgtcac cggcttcccc      480
gcctaccacc agggcttcgg cccctccctc ccggacgtcg acttcctgac cccgccgcag      540
ccctaccgcc gggagctgtt cgccggttcc gacgtcaccg acttctgcct cgccgaactg      600
cgcgagacca tcgaccggat cggcccggag cggatcgcgg cgatgatcgg cgagccgatc      660
```

<210> SEQ ID NO 8
<211> LENGTH: 25
<212> TYPE: DNA
<213> ORGANISM: Streptomyces clavuligerus

<400> SEQUENCE: 8

```
ctgacgctgc aggaggaagt cccgc                                             25
```

<210> SEQ ID NO 9
<211> LENGTH: 25
<212> TYPE: DNA
<213> ORGANISM: Streptomyces clavuligerus

<400> SEQUENCE: 9

```
cggggcgagg acgtcgtccc gatcc                                             25
```

<210> SEQ ID NO 10
<211> LENGTH: 25
<212> TYPE: DNA
<213> ORGANISM: Streptomyces clavuligerus -continued

```
<400> SEQUENCE: 10
gagcccctgg acgtcggcgg tgtcc                                           25

<210> SEQ ID NO 11
<211> LENGTH: 25
<212> TYPE: DNA
<213> ORGANISM: Streptomyces clavuligerus

<400> SEQUENCE: 11
gacggtgcat gctcagcagg gagcg                                           25

<210> SEQ ID NO 12
<211> LENGTH: 972
<212> TYPE: DNA
<213> ORGANISM: Streptomyces clavuligerus

<400> SEQUENCE: 12
atgacctcag tggactgcac cgcgtacggc cccgagctgc gcgcgctcgc cgcccggctg     60
ccccggaccc ccgggccga cctgtacgcc ttcctggacg ccgcgcacac agccgccgcc    120
tcgctccccg cgccctcgc caccgcgctg acaccttca cgccgaggg cagcgaggac     180 ggccatctgc tgctgcgcgg cctcccggtg gaggccgacg ccgacctccc caccaccccg    240
agcagcaccc cggcgcccga ggaccgctcc ctgctgacca tggaggccat gctcggactg    300
gtgggccgcc ggctcggtct gcacacgggg taccgggagc tgcgctcggg cacggtctac    360
cacgacgtgt accgtcgcc cggcgcgcac cacctgtcct cggagacctc cgagacgctg    420
ctggagttcc acacggagat ggcctaccac cggctccagc cgaactacgt catgctggcc    480
tgctcccggg ccgaccacga gcgcacggcg gccacactcg tcgcctcggt ccgcaaggcg    540
ctgcccctgc tggacgagag gacccgggcc cggctcctcg accggaggat gccctgctgc    600
gtggatgtgg ccttccgcgg cggggtggac gacccgggcg ccatcgccca ggtcaaaccg    660
ctctacgggg acgcggacga tcccttcctc gggtacgacc gcgagctgct ggcgccggag    720
gaccccgcgg acaaggaggc cgtcgccgcc ctgtccaagg cgctcgacga ggtcacggag    780
gcggtgtatc tggagcccgg cgatctgctg atcgtcgaca acttccgcac cacgcacgcg    840
cggacgccgt tctcgccccg ctgggacggg aaggaccgct ggctgcaccg cgtctacatc    900
cgcaccgacc gcaatggaca gctctccggc ggcgagcgcg cgggcgacgt cgtcgccttc    960
acaccgcgcg gc                                                       972

<210> SEQ ID NO 13
<211> LENGTH: 48
<212> TYPE: PRT
<213> ORGANISM: Streptomyces clavuligerus

<400> SEQUENCE: 13

Met Thr Arg Pro Pro Gly Leu Ser Ala His Thr His Gly Ser Val Ser
 1               5                  10                  15

Gly Ser Leu Leu Arg Arg Val Ala Gly His Tyr Pro Thr Gly Val Val
            20                  25                  30

Leu Val Thr Gly Pro Ala Glu Ala Pro Gly Gln Pro Pro Ala Met
        35                  40                  45

<210> SEQ ID NO 14
<211> LENGTH: 151
<212> TYPE: PRT
<213> ORGANISM: Streptomyces clavuligerus
```

```
<400> SEQUENCE: 14

Met Ser Val Ala Ser Gly Met Thr Asp Glu Gln Arg Lys Ala Val
1               5                   10                  15

Ile Thr Ala Tyr Phe Lys Ala Phe Asp Asn Gly Gly Val Gly Ser Asp
            20                  25                  30

Gly Thr Pro Ala Ile Asp Tyr Phe Ala Glu Asp Ala Val Phe Phe Phe
            35                  40                  45

Pro Lys Trp Gly Leu Ala Arg Gly Lys Ser Glu Ile Ala Arg Leu Phe
50                  55                  60

Asp Asp Leu Gly Gly Thr Ile Arg Ser Ile Thr His His Leu Trp Ser
65                  70                  75                  80

Val Asn Trp Ile Leu Thr Gly Thr Glu Leu Leu Ala Ala Glu Gly Thr
                85                  90                  95

Thr His Gly Glu His Arg Asp Gly Pro Trp Arg Ala Gly Asp Pro Glu
            100                 105                 110

Trp Ala Ala Gly Arg Trp Cys Thr Val Tyr Glu Val Arg Asp Phe Leu
            115                 120                 125

Val His Arg Ala Phe Val Tyr Leu Asp Pro Asp Tyr Ala Gly Lys Asp
            130                 135                 140

Thr Ala Arg Tyr Pro Trp Leu
145                 150

<210> SEQ ID NO 15
<211> LENGTH: 344
<212> TYPE: PRT
<213> ORGANISM: Streptomyces clavuligerus

<400> SEQUENCE: 15

Met Ser Arg Ser Pro Glu Ser Pro Ala Gly Ser Val Ser Ala Ala
1               5                   10                  15

Val Pro Arg Pro Pro Val Arg Ala Leu Arg Asp Leu Pro Val Ser Ala
            20                  25                  30

Gln Gly Leu Gly Cys Leu Pro Thr Thr Asp Phe Tyr Gly Arg Pro Asp
            35                  40                  45

Arg Ala Arg Ala Thr Ala Thr Ile Arg Ala Ala Val Asp Ala Gly Val
50                  55                  60

Thr Leu Leu Asp Thr Ala Asp Val Gln Gly Leu Gly Ala Gly Glu Glu
65                  70                  75                  80

Leu Leu Gly Arg Ala Val Ala Gly Arg Arg Asp Glu Val Leu Ile Ala
                85                  90                  95

Thr Lys Phe Gly Met Val Arg Ser Ser Asp Gly Ala Ser Gln Gly Leu
            100                 105                 110

Cys Gly Glu Pro Ser Tyr Val Arg Ala Ala Cys Glu Arg Ser Leu Arg
            115                 120                 125

Arg Leu Gly Thr Asp Arg Ile Asp Leu Tyr Tyr Gln His Trp Thr Asp
            130                 135                 140

Pro Ala Val Pro Ile Glu Glu Thr Val Gly Ala Val Ala Glu Leu Val
145                 150                 155                 160

Arg Glu Gly Lys Val Arg Arg Leu Gly Leu Ser Glu Pro Ser Ala Ala
                165                 170                 175

Thr Leu Arg Arg Ala Asp Ala Val His Pro Val Thr Ala Val Gln Ser
            180                 185                 190

Glu Trp Ser Leu Trp Ser Arg Gly Ile Glu Asp Glu Val Val Pro Val
            195                 200                 205
```

```
Cys Arg Glu Leu Gly Ile Gly Ile Val Ala Tyr Ala Pro Leu Gly Arg
    210                 215                 220

Gly Phe Leu Thr Gly Thr Ile Arg Thr Thr Asp Asp Leu Gly Asp Glu
225                 230                 235                 240

Asp Phe Arg Arg Gly Gln Pro Arg Phe Ser Ala Pro Ala Leu Ala Arg
                245                 250                 255

Asn Arg Ser Leu Leu His Arg Leu Arg Pro Val Ala Asp Gly Leu Gly
            260                 265                 270

Leu Thr Leu Ala Gln Leu Ala Leu Ala Trp Leu His His Arg Gly Glu
        275                 280                 285

Asp Val Val Pro Ile Pro Gly Thr Ala Asn Pro Ala His Leu Ala Asp
    290                 295                 300

Asn Leu Ala Ala Ala Ser Ile Arg Leu Asp Asp Arg Ser Leu Ala Glu
305                 310                 315                 320

Val Thr Ala Ala Ile Ser His Pro Val Ser Gly Glu Arg Tyr Thr Pro
                325                 330                 335

Ala Leu Leu Ala Met Ile Gly Asn
            340

<210> SEQ ID NO 16
<211> LENGTH: 328
<212> TYPE: PRT
<213> ORGANISM: Streptomyces clavuligerus

<400> SEQUENCE: 16

Met Glu Cys Arg Ile Phe Glu Ile Asp Glu Leu Pro Leu Leu Asp Gly
  1               5                  10                  15

Glu Val Leu Arg Asp Ala Arg Ile Gly Tyr Ala Met Tyr Gly Thr Pro
                 20                  25                  30

Asn Ala Asp Gly Thr Asn Val Val Leu Cys Pro Ser Phe Phe Gly Arg
             35                  40                  45

Asp His Thr Gly Tyr Asp Trp Leu Ile Gly Ala Gly Leu Pro Leu Asp
         50                  55                  60

Thr Arg Arg Tyr Cys Val Val Thr Ala Gly Leu Phe Gly Asn Gly Val
 65                  70                  75                  80

Ser Ser Ser Pro Gly Asn His Pro Ser Gly Ser Arg Phe Pro Leu Ile
                 85                  90                  95

Thr Pro Gln Asp Asn Val Ala Ala Gln His Arg Leu Leu Thr Glu Glu
            100                 105                 110

Leu Gly Val Arg Glu Leu Ala Leu Val Thr Gly Trp Ser Met Gly Ala
        115                 120                 125

Ala His Ala Tyr Gln Trp Ala Val Ser His Pro Gly Met Val Arg Arg
    130                 135                 140

Ile Ala Pro Ile Cys Gly Ala Pro Val Ser Ser Pro His Ser Leu Val
145                 150                 155                 160

Leu Leu Ser Gly Leu Ala Ala Leu Ser Ala Asp Ala Gly Glu Arg
                165                 170                 175

Gly Arg Lys Ala Ala Gly Arg Val Phe Ala Gly Trp Gly Thr Ser Arg
            180                 185                 190

Ser Phe Trp Ala Arg Arg Ala His Arg Glu Leu Gly Phe Ala Thr Arg
        195                 200                 205

Glu Glu Tyr Leu Thr Gly Phe Trp Glu Gln Val Phe Leu Ser Gly Pro
    210                 215                 220

Gly Ala Ala Asp Leu Leu Thr Met Val Arg Thr Trp Glu Asn Thr Asp
225                 230                 235                 240
```

```
Val Gly Ala Thr Pro Gly Ala Gly Ser Val Glu Ala Ala Leu Ala
                245                 250                 255

Ser Val Thr Ala Arg Ala Val Val Leu Pro Gly Ala Leu Asp Val Cys
                260                 265                 270

Phe Ala Val Glu Asp Glu Lys Arg Val Ala Asp Leu Leu Pro Tyr Ala
                275                 280                 285

Ser Leu Glu Val Ile Pro Gly Val Trp Gly His Leu Ala Gly Ser Gly
                290                 295                 300

Gly Ser Ala Ala Asp Arg Glu Phe Ile Gly Ala Leu Arg Arg Leu
305                 310                 315                 320

Leu Asp Ser Pro Val Asp Gly Gly
                325

<210> SEQ ID NO 17
<211> LENGTH: 394
<212> TYPE: PRT
<213> ORGANISM: Streptomyces clavuligerus

<400> SEQUENCE: 17

Met Lys Ser Ile Leu Phe Tyr Leu Pro Thr Val Gly Ser His Ala Gln
  1               5                  10                  15

Val Gln Arg Gly Met Ala Gly Val Asn Pro Gln Asn Tyr Gln Asn Met
                 20                  25                  30

Leu Arg Gln Leu Thr Arg Gln Ala Gln Ala Asp Glu Leu Gly Tyr
             35                  40                  45

Trp Gly Leu Ser Phe Thr Glu His His Phe His Thr Glu Gly Phe Glu
 50                  55                  60

Val Ser Asn Asn Pro Ile Met Leu Gly Leu Tyr Leu Gly Met Gln Thr
 65                  70                  75                  80

Arg His Ile Arg Val Gly Gln Met Ala Asn Val Leu Pro Leu His Asn
                 85                  90                  95

Pro Leu Arg Leu Ala Glu Asp Leu Ala Met Leu Asp His Met Thr Arg
                100                 105                 110

Gly Arg Ala Phe Val Gly Ile Ala Arg Gly Phe Gln Lys Arg Trp Ala
                115                 120                 125

Asp Ile Met Gly Gln Val Tyr Gly Val Gly Gly Thr Leu Ser Asp Ala
            130                 135                 140

Gly Glu Arg Asp Arg Arg Asn Arg Ala Leu Phe Glu Glu His Trp Glu
145                 150                 155                 160

Ile Ile Lys Lys Ala Trp Thr Thr Glu Thr Phe Thr His Ser Gly Glu
                165                 170                 175

Gln Trp Thr Ile Pro Val Pro Asp Leu Glu Phe Pro Tyr Glu Ala Val
                180                 185                 190

Arg Arg Tyr Gly Arg Gly Leu Asp Glu Asn Gly Val Ile Arg Glu Val
                195                 200                 205

Gly Ile Ala Pro Lys Pro Tyr Gln Arg Pro His Pro Pro Val Phe Gln
            210                 215                 220

Pro Phe Ser Phe Ser Glu Asp Thr Phe Arg Phe Cys Ala Arg Glu Gly
225                 230                 235                 240

Val Val Pro Ile Leu Met Asn Thr Asp Gln Ile Val Ala Arg Leu
                245                 250                 255

Met Asp Ile Tyr Arg Glu Glu Ala Glu Ala Ala Gly His Gly Thr Leu
            260                 265                 270

Arg Arg Gly Glu Arg Val Gly Val Met Lys Asp Val Leu Val Ser Arg
```

-continued

```
                275                 280                 285
Asp Ser Gly Glu Ala His His Trp Ala Ser Arg Gly Gly Phe Ile
            290                 295                 300

Phe Glu Asn Trp Phe Gly Pro Met Gly Phe Thr Glu Ala Leu Arg Ala
305                 310                 315                 320

Thr Gly Glu Thr Gly Pro Ile Gly Ser Asp Tyr Lys Thr Leu Val Asp
                325                 330                 335

Arg Gly Leu Glu Trp Val Gly Thr Pro Asp Asp Ile Asn Arg Met Ile
            340                 345                 350

Glu Lys Leu Val Glu Arg His Asp Pro Glu Tyr Leu Leu Gln Cys Gln
            355                 360                 365

Tyr Ser Gly Leu Ile Pro His Asp Val Gln Leu Arg Ser Leu Glu Leu
        370                 375                 380

Trp Ala Thr Glu Ile Ala Pro Asn Trp Leu
385                 390

<210> SEQ ID NO 18
<211> LENGTH: 220
<212> TYPE: PRT
<213> ORGANISM: Streptomyces clavuligerus

<400> SEQUENCE: 18

Met Pro Gly Ser Gly Leu Glu Ala Leu Asp Arg Ala Thr Leu Ile His
  1               5                  10                  15

Pro Thr Leu Ser Gly Asn Thr Ala Glu Arg Ile Val Leu Thr Ser Gly
             20                  25                  30

Ser Gly Ser Arg Val Arg Asp Thr Asp Gly Arg Glu Tyr Leu Asp Ala
         35                  40                  45

Ser Ala Val Leu Gly Val Thr Gln Val Gly His Gly Arg Ala Glu Leu
 50                  55                  60

Ala Arg Val Ala Ala Glu Gln Met Ala Arg Leu Glu Tyr Phe His Thr
 65                  70                  75                  80

Trp Gly Thr Ile Ser Asn Asp Arg Ala Val Glu Leu Ala Ala Arg Leu
                 85                  90                  95

Val Gly Leu Ser Pro Glu Pro Leu Thr Arg Val Tyr Phe Thr Ser Gly
            100                 105                 110

Gly Ala Glu Gly Asn Glu Ile Ala Leu Arg Met Ala Arg Leu Tyr His
        115                 120                 125

His Arg Arg Gly Glu Ser Ala Arg Thr Trp Ile Leu Ser Arg Arg Ser
    130                 135                 140

Ala Tyr His Gly Val Gly Tyr Gly Ser Gly Gly Val Thr Gly Phe Pro
145                 150                 155                 160

Ala Tyr His Gln Gly Phe Gly Pro Ser Leu Pro Asp Val Asp Phe Leu
                165                 170                 175

Thr Pro Pro Gln Pro Tyr Arg Arg Glu Leu Phe Ala Gly Ser Asp Val
            180                 185                 190

Thr Asp Phe Cys Leu Ala Glu Leu Arg Glu Thr Ile Asp Arg Ile Gly
        195                 200                 205

Pro Glu Arg Ile Ala Ala Met Ile Gly Glu Pro Ile
    210                 215                 220

<210> SEQ ID NO 19
<211> LENGTH: 324
<212> TYPE: PRT
<213> ORGANISM: Streptomyces clavuligerus
```

-continued

```
<400> SEQUENCE: 19

Met Thr Ser Val Asp Cys Thr Ala Tyr Gly Pro Glu Leu Arg Ala Leu
1               5                   10                  15

Ala Ala Arg Leu Pro Arg Thr Pro Arg Ala Asp Leu Tyr Ala Phe Leu
            20                  25                  30

Asp Ala Ala His Thr Ala Ala Ala Ser Leu Pro Gly Ala Leu Ala Thr
        35                  40                  45

Ala Leu Asp Thr Phe Asn Ala Glu Gly Ser Glu Asp Gly His Leu Leu
    50                  55                  60

Leu Arg Gly Leu Pro Val Glu Ala Asp Ala Asp Leu Pro Thr Thr Pro
65                  70                  75                  80

Ser Ser Thr Pro Ala Pro Glu Asp Arg Ser Leu Leu Thr Met Glu Ala
                85                  90                  95

Met Leu Gly Leu Val Gly Arg Arg Leu Gly Leu His Thr Gly Tyr Arg
                100                 105                 110

Glu Leu Arg Ser Gly Thr Val Tyr His Asp Val Tyr Pro Ser Pro Gly
            115                 120                 125

Ala His His Leu Ser Ser Glu Thr Ser Glu Thr Leu Leu Glu Phe His
        130                 135                 140

Thr Glu Met Ala Tyr His Arg Leu Gln Pro Asn Tyr Val Met Leu Ala
145                 150                 155                 160

Cys Ser Arg Ala Asp His Glu Arg Thr Ala Ala Thr Leu Val Ala Ser
                165                 170                 175

Val Arg Lys Ala Leu Pro Leu Leu Asp Glu Arg Thr Arg Ala Arg Leu
                180                 185                 190

Leu Asp Arg Arg Met Pro Cys Cys Val Asp Val Ala Phe Arg Gly Gly
            195                 200                 205

Val Asp Asp Pro Gly Ala Ile Ala Gln Val Lys Pro Leu Tyr Gly Asp
            210                 215                 220

Ala Asp Asp Pro Phe Leu Gly Tyr Asp Arg Glu Leu Leu Ala Pro Glu
225                 230                 235                 240

Asp Pro Ala Asp Lys Glu Ala Val Ala Ala Leu Ser Lys Ala Leu Asp
                245                 250                 255

Glu Val Thr Glu Ala Val Tyr Leu Glu Pro Gly Asp Leu Leu Ile Val
                260                 265                 270

Asp Asn Phe Arg Thr Thr His Ala Arg Thr Pro Phe Ser Pro Arg Trp
            275                 280                 285

Asp Gly Lys Asp Arg Trp Leu His Arg Val Tyr Ile Arg Thr Asp Arg
            290                 295                 300

Asn Gly Gln Leu Ser Gly Gly Glu Arg Ala Gly Asp Val Val Ala Phe
305                 310                 315                 320

Thr Pro Arg Gly
```

The invention claimed is:

1. A process for improving clavulanic acid production in a *S. clavuligerus* comprising partially or completely deleting, or disrupting by insertional inactivation DNA, of one or more open reading frames in the *S. clavuligerus* wherein said one or more open reading frame is selected from the group consisting of: orfup1 (SEQ ID NO: 4), orfdwn1 (SEQ ID NO: 5), orfdwn2 (SEQ ID NO: 6) and orfdwn3 (SEQ ID NO: 7).

2. The process of claim 1 comprising disrupting or otherwise making defective DNA regions flanking cas1.

3. The process of claim 1 wherein said open reading frame is orfup1 (SEQ ID NO: 4).

* * * * *